United States Patent
Beck et al.

(10) Patent No.: US 8,425,470 B2
(45) Date of Patent: Apr. 23, 2013

(54) ANTI-FREE-FLOW MECHANISM FOR ENTERAL FEEDING PUMPS

(75) Inventors: Kent Beck, Layton, UT (US); Philip Eggers, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 88 days.

(21) Appl. No.: 12/896,729

(22) Filed: Oct. 1, 2010

(65) Prior Publication Data

US 2011/0082438 A1    Apr. 7, 2011

Related U.S. Application Data

(63) Continuation-in-part of application No. 12/416,041, filed on Mar. 31, 2009.

(60) Provisional application No. 61/041,561, filed on Apr. 1, 2008.

(51) Int. Cl.
*A61M 39/00*    (2006.01)

(52) U.S. Cl.
USPC ........... 604/250; 604/246; 604/256; 137/853; 251/342

(58) Field of Classification Search .................. 604/151, 604/246, 250; 251/342; 137/853; 417/477.2
See application file for complete search history.

(56) References Cited

U.S. PATENT DOCUMENTS

| | | | |
|---|---|---|---|
| 584,091 A | 6/1897 | Leidich | |
| 1,238,521 A | 8/1917 | Janish, Jr. | |
| 2,471,623 A | 5/1949 | Hubbell | |
| 2,518,165 A | 8/1950 | Millard | |
| 2,858,095 A | 10/1958 | Harris et al. | |
| 2,999,499 A | 11/1961 | Willet | |
| 3,213,882 A | 10/1965 | Beatty | |
| 3,329,391 A | 7/1967 | Deane | |
| D208,753 S | 9/1967 | Curry | |
| 3,497,175 A | 2/1970 | Koland | |
| 3,707,972 A | 1/1973 | Villari et al. | |
| 3,985,140 A | 10/1976 | Harris | |
| 3,998,364 A | 12/1976 | Hollander | |
| 4,037,596 A | 7/1977 | LeFevre et al. | |
| 4,063,555 A | 12/1977 | Ulinder | |
| 4,065,093 A | 12/1977 | Phillips | |
| 4,106,675 A | 8/1978 | Taylor | |
| 4,142,645 A | 3/1979 | Walton | |
| 4,160,383 A | 7/1979 | Rauschenberger | |

(Continued)

FOREIGN PATENT DOCUMENTS

| | | |
|---|---|---|
| EP | 0 150 666 | 9/1984 |
| EP | 0 276 356 | 8/1988 |

(Continued)

OTHER PUBLICATIONS

WIPO, International Searching Authority ISA/KR, International Search Report issued May 4, 2012 in International Application No. PCT/US2011/054077.

*Primary Examiner* — Emily Schmidt
(74) *Attorney, Agent, or Firm* — Hodgson Russ LLP

(57) ABSTRACT

An anti-free-flow mechanism includes an occluder mechanism which is disposed along a segment of tubing. The occluder mechanism is normally in a biased closed position, but may be moved into an open position by moving an engagement member into engagement with the tubing segment to deform the tubing segment and open a flow channel. Unless force is applied to keep the engagement member in contact with the tubing segment, the tubing will return to the first, closed position.

22 Claims, 34 Drawing Sheets

U.S. PATENT DOCUMENTS

| | | | |
|---|---|---|---|
| 4,230,151 A | 10/1980 | Jonsson |
| 4,236,880 A | 12/1980 | Archibald |
| 4,300,571 A | 11/1981 | Waldbillig |
| 4,373,524 A | 2/1983 | Leibinsohn |
| 4,381,591 A | 5/1983 | Barger et al. |
| 4,382,453 A | 5/1983 | Bujan et al. |
| 4,425,116 A | 1/1984 | Bilstad et al. |
| 4,430,073 A | 2/1984 | Bemis et al. |
| 4,453,295 A | 6/1984 | Laszczower |
| 4,498,843 A | 2/1985 | Schneider et al. |
| 4,524,802 A | 6/1985 | Lawrence et al. |
| 4,527,588 A | 7/1985 | Tseo et al. |
| 4,559,036 A | 12/1985 | Wunsch |
| 4,559,045 A | 12/1985 | Danby et al. |
| 4,579,553 A | 4/1986 | Urquhart et al. |
| 4,596,557 A | 6/1986 | Pexa |
| 4,624,663 A | 11/1986 | Danby et al. |
| 4,634,092 A | 1/1987 | Daniell et al. |
| 4,645,489 A | 2/1987 | Krumme et al. |
| 4,689,043 A | 8/1987 | Bisha |
| 4,728,324 A | 3/1988 | Steigerwald et al. |
| 4,730,635 A | 3/1988 | Linden |
| 4,787,406 A | 11/1988 | Edwards et al. |
| 4,913,401 A | 4/1990 | Handke |
| 4,932,629 A | 6/1990 | Rodomista et al. |
| 4,932,938 A | 6/1990 | Goldberg et al. |
| 4,935,010 A | 6/1990 | Cox et al. |
| 4,960,259 A | 10/1990 | Sunnanvader et al. |
| 5,017,192 A | 5/1991 | Dodge et al. |
| 5,020,562 A | 6/1991 | Richmond et al. |
| 5,022,422 A | 6/1991 | di Palma |
| 5,029,621 A | 7/1991 | Lewis |
| 5,083,561 A | 1/1992 | Russo |
| 5,098,406 A | 3/1992 | Sawyer |
| 5,151,019 A | 9/1992 | Danby et al. |
| 5,219,327 A | 6/1993 | Okada |
| 5,232,193 A | 8/1993 | Skakoon |
| 5,238,218 A | 8/1993 | Mackal |
| 5,254,083 A | 10/1993 | Gentelia et al. |
| 5,257,978 A | 11/1993 | Haber et al. |
| 5,265,847 A | 11/1993 | Vorhis |
| 5,336,174 A | 8/1994 | Daoud et al. |
| 5,351,932 A | 10/1994 | Von Herrmann |
| 5,391,144 A | 2/1995 | Sakurai et al. |
| 5,395,351 A | 3/1995 | Munsch |
| 5,396,925 A | 3/1995 | Poli |
| 5,437,642 A | 8/1995 | Thill et al. |
| 5,438,868 A | 8/1995 | Holden et al. |
| 5,456,887 A | 10/1995 | Calvo et al. |
| 5,474,544 A | 12/1995 | Lynn |
| 5,482,446 A | 1/1996 | Williamson et al. |
| 5,514,102 A | 5/1996 | Winterer et al. |
| 5,531,680 A | 7/1996 | Dumas et al. |
| 5,531,713 A | 7/1996 | Mastronardi et al. |
| 5,556,386 A | 9/1996 | Todd |
| 5,578,070 A | 11/1996 | Utterberg |
| D389,228 S | 1/1998 | Winterer et al. |
| 5,704,584 A | 1/1998 | Winterer et al. |
| 5,720,721 A | 2/1998 | Dumas et al. |
| 5,733,061 A | 3/1998 | Child |
| 5,746,756 A | 5/1998 | Bromfield et al. |
| 5,789,675 A | 8/1998 | Blaine et al. |
| 5,807,312 A | 9/1998 | Dzwonkiewicz |
| 5,810,323 A | 9/1998 | Winterer et al. |
| 5,826,621 A | 10/1998 | Jemmott |
| 5,971,357 A | 10/1999 | Denton et al. |
| 6,017,332 A | 1/2000 | Urrutia |
| 6,023,970 A | 2/2000 | Blaine |
| 6,048,331 A | 4/2000 | Tsugita et al. |
| 6,092,695 A | 7/2000 | Loeffler |
| 6,129,699 A | 10/2000 | Haight et al. |
| 6,142,979 A | 11/2000 | McNally et al. |
| RE37,074 E | 2/2001 | Danby et al. |
| 6,183,447 B1 | 2/2001 | Urrutia |
| 6,192,752 B1 | 2/2001 | Blaine |
| 6,196,922 B1 | 3/2001 | Hantschk et al. |
| 6,196,992 B1 | 3/2001 | Keilman et al. |
| 6,209,538 B1 | 4/2001 | Casper et al. |
| 6,261,262 B1 | 7/2001 | Briggs et al. |
| 6,328,720 B1 | 12/2001 | McNally |
| D455,489 S | 4/2002 | Beck et al. |
| 6,398,758 B1 | 6/2002 | Jacobsen et al. |
| 6,398,780 B1 | 6/2002 | Farley et al. |
| 6,461,335 B1 | 10/2002 | Noecker |
| 6,494,864 B1 | 12/2002 | Kerwin et al. |
| 6,506,035 B1 | 1/2003 | Beck et al. |
| 6,523,414 B1 | 2/2003 | Malmstrom et al. |
| 6,531,708 B1 | 3/2003 | Malmstrom et al. |
| RE38,145 E | 6/2003 | Lynn |
| 6,595,950 B1 | 7/2003 | Miles et al. |
| 6,623,447 B2 | 9/2003 | Miles et al. |
| 6,636,010 B1 | 10/2003 | Malmstrom et al. |
| H2090 H | 11/2003 | Walker |
| 6,659,976 B2 | 12/2003 | Beck et al. |
| 6,685,670 B2 | 2/2004 | Miles et al. |
| 6,749,591 B1 | 6/2004 | McNally et al. |
| 6,750,468 B2 | 6/2004 | Malmstrom et al. |
| D501,924 S | 2/2005 | Cise et al. |
| 6,852,094 B2 | 2/2005 | Beck et al. |
| D503,799 S | 4/2005 | Beck |
| D503,978 S | 4/2005 | Beck |
| D504,506 S | 4/2005 | Beck et al. |
| D505,199 S | 5/2005 | Beck et al. |
| 6,902,541 B2 | 6/2005 | McNally et al. |
| 6,907,788 B2 | 6/2005 | Malmstrom et al. |
| D507,647 S | 7/2005 | Beck et al. |
| 6,923,785 B2 | 8/2005 | Miles et al. |
| 6,949,376 B2 | 9/2005 | Kluttz et al. |
| 6,979,311 B2 | 12/2005 | Miles et al. |
| 7,037,302 B2 | 5/2006 | Vaillancourt |
| D523,553 S | 6/2006 | Beck et al. |
| 7,070,575 B2 | 7/2006 | Beck et al. |
| 7,121,143 B2 | 10/2006 | Malmstrom et al. |
| 7,150,727 B2 | 12/2006 | Cise et al. |
| D536,783 S | 2/2007 | Cise et al. |
| 7,367,963 B2 | 5/2008 | Cise et al. |
| 2002/0169424 A1 | 11/2002 | Miles et al. |
| 2004/0097885 A1 | 5/2004 | Beck et al. |
| 2004/0220542 A1 | 11/2004 | Cise et al. |
| 2004/0260332 A1 | 12/2004 | Dubrul et al. |
| 2005/0004540 A1 | 1/2005 | McNally et al. |
| 2005/0119625 A1 | 6/2005 | Miles et al. |
| 2006/0058740 A1 | 3/2006 | Cise |
| 2007/0118078 A1 | 5/2007 | McNally |
| 2007/0151346 A1 | 7/2007 | Malmstrom et al. |
| 2008/0065008 A1 | 3/2008 | Barbut et al. |
| 2008/0098798 A1 | 5/2008 | Riley |
| 2008/0103445 A1 | 5/2008 | Blaine et al. |
| 2008/0119782 A1 | 5/2008 | Steinman |
| 2008/0134750 A1 | 6/2008 | Riley |
| 2008/0208117 A1 | 8/2008 | Steinman |
| 2008/0276911 A1 | 11/2008 | Woody |
| 2009/0049919 A1 | 2/2009 | Hills |
| 2009/0149801 A1 | 6/2009 | Crandall |
| 2009/0254034 A1 | 10/2009 | Beck |
| 2010/0082001 A1 | 4/2010 | Beck et al. |
| 2011/0028899 A1 | 2/2011 | Beck et al. |

FOREIGN PATENT DOCUMENTS

| | | |
|---|---|---|
| EP | 0 423 978 | 10/1990 |
| EP | 0 483 794 | 10/1991 |
| GB | 2 338 759 | 12/1999 |
| WO | WO 96/08666 | 3/1996 |
| WO | WO 96-17636 | 6/1996 |

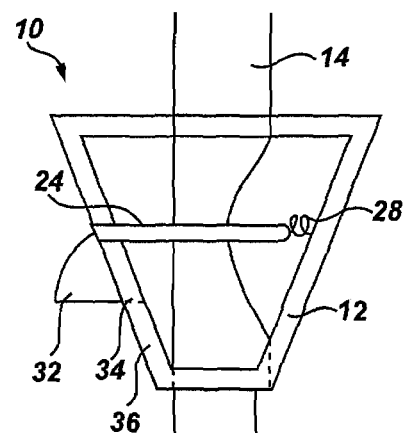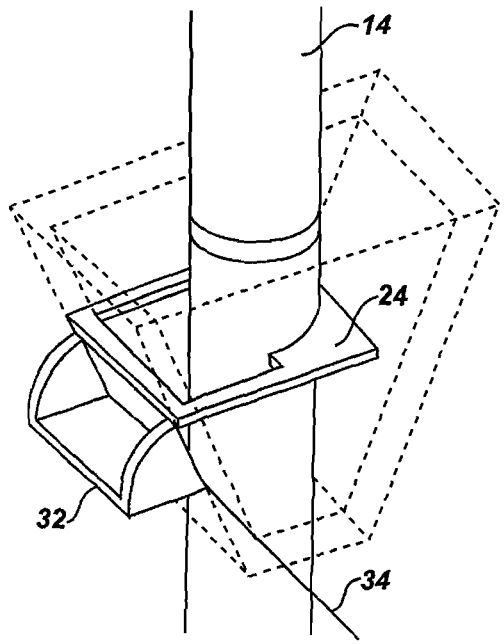
Fig. 2B
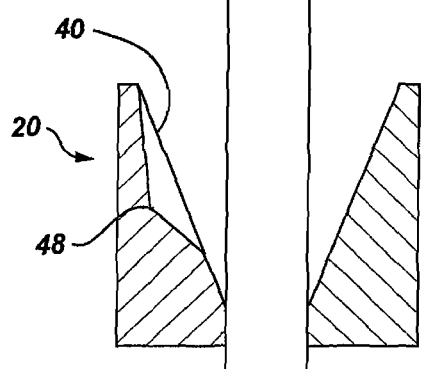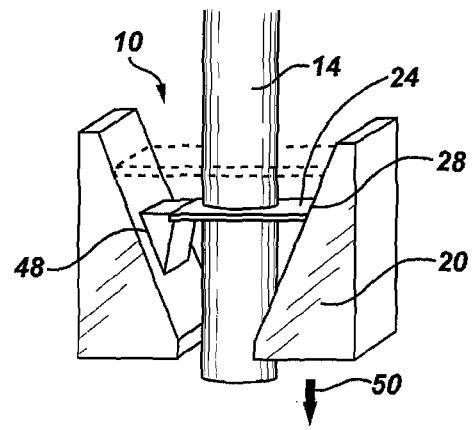
Fig. 2A
Fig. 2C

SECTION A-A

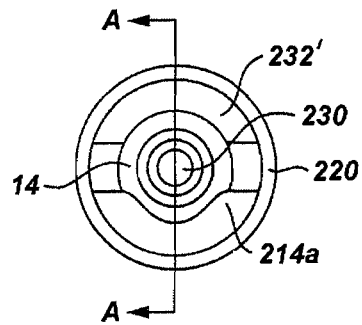
Fig. 9B
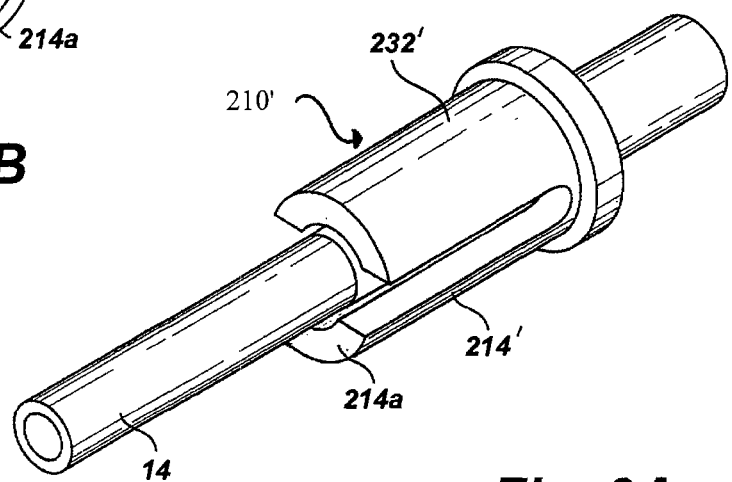
Fig. 9A
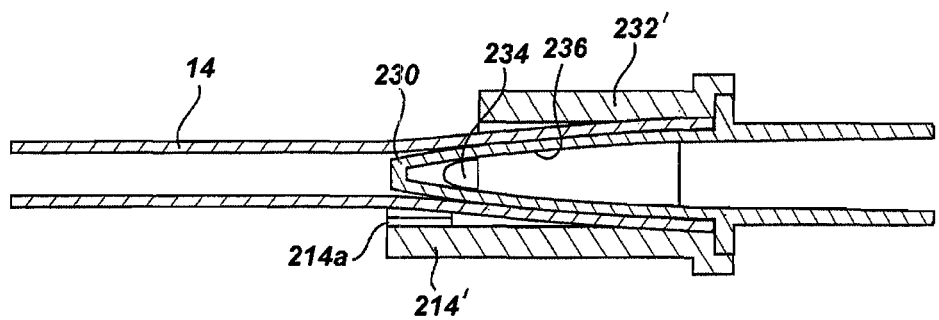
Fig. 9C  SECTION A-A

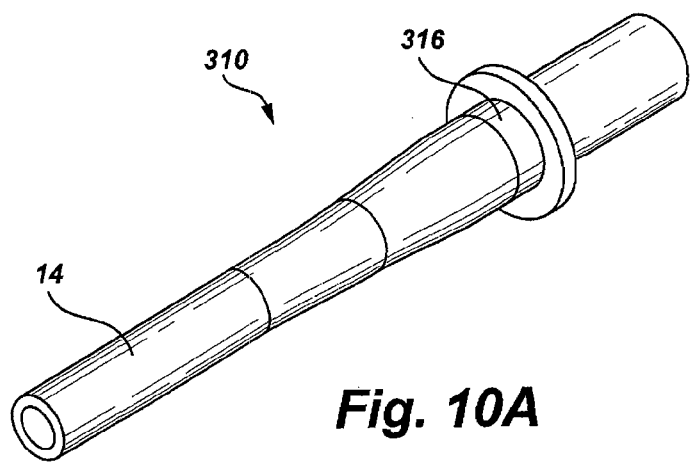
Fig. 10A
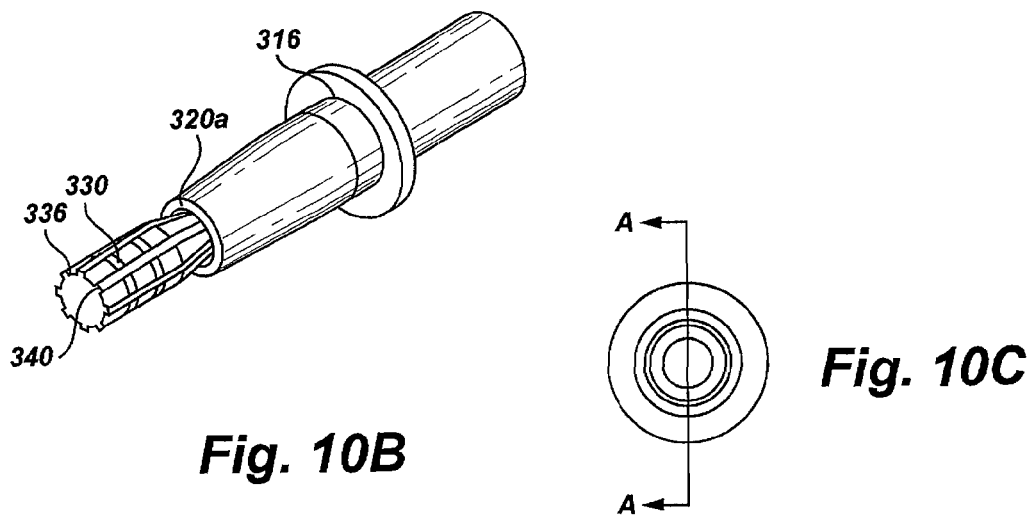
Fig. 10B
Fig. 10C

SECTION A-A

SECTION A-A

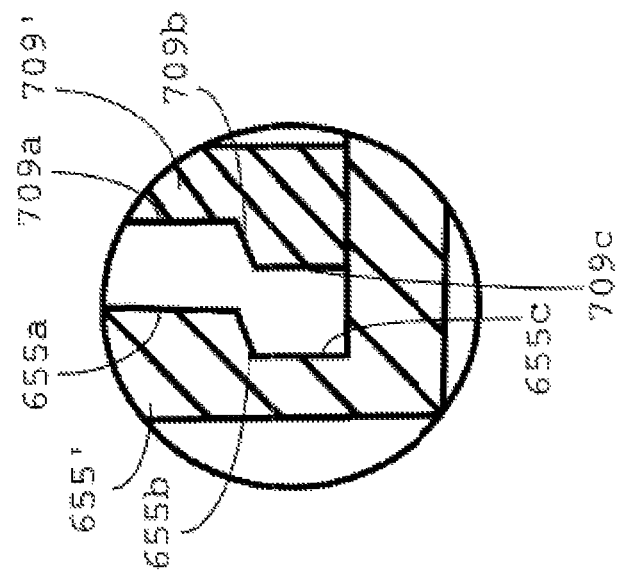
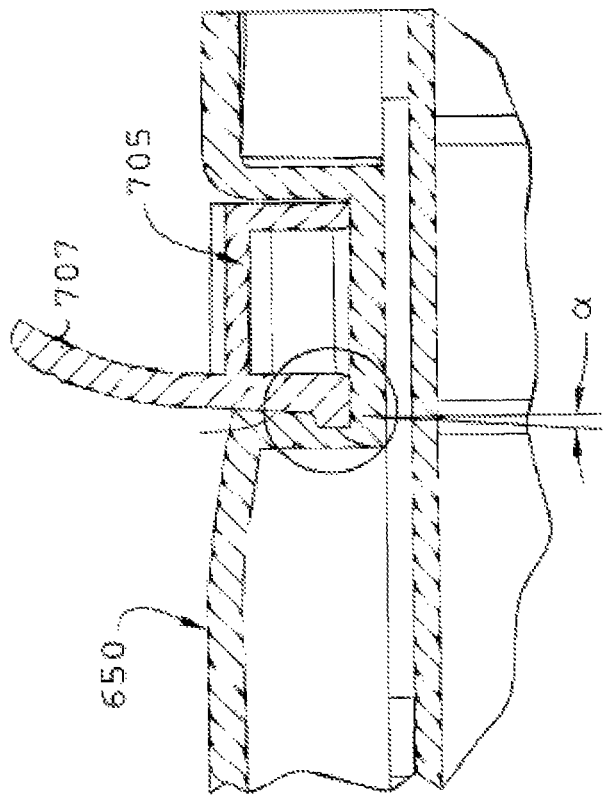
FIG. 33
FIG. 34

# ANTI-FREE-FLOW MECHANISM FOR ENTERAL FEEDING PUMPS

PRIORITY

This application is a continuation-in-part of U.S. patent application Ser. No. 12/416,041, filed Mar. 31, 2009, which is incorporated in its entirety, and claims priority to U.S. Provisional Patent Application No. 61/041,561, filed Apr. 1, 2008, which is incorporated herein by reference in its entirety.

FIELD

The present invention relates to peristaltic pumps and cassettes which may be used in peristaltic pumps to selectively control fluid flow and prevent free-flow situations.

BACKGROUND

There are numerous environments in which peristaltic pumps are used to deliver fluids. Peristaltic pumps are often advantageous because of their ability to deliver relatively accurate doses and to deliver metered doses over a prolonged period of time. Peristaltic pumps may be used to dispense liquids in laboratories, to regulate fluid flow in automobiles, and are frequently used in the medical field to deliver fluids to a patient. These fluids may be those which are delivered to the digestive tract, commonly referred to as "enteral" applications, or to into the venous system, commonly referred to as "parenteral" applications.

There are many different types of enteral feeding devices, including nasogastric, esophagastric, and abdominal feeding apparatus for supplying nutritional products to patients. These nutritional products, which are almost always flowable, are available for a variety of supplanting and supplemental feeding requirements.

Likewise, there are many different types of parenteral infusion devices which deliver IV solutions, medication and some forms of nutrition to patients. Each system has relative advantages and disadvantages depending on the context.

Conventional infusion and feeding apparatuses, whether for enteral or parenteral applications, typically include a pump and various components and/or accessories for transferring the nutritional product or IV solution from a container (e.g., a bottle or bag) into the digestive tract or venous system, respectively, of a patient. These components, which may be reusable or disposable, typically include various tubing and connectors. All of the components (e.g., tubing and connectors) necessary for transferring the nutritional product or IV solution to a patient using a specific pump, are often collectively referred to as a "feeding set" or an "infusion set." For ease of references, infusion sets and feeding sets will be referred to herein as a "feeding set" or "feeding sets" and it shall be understood that such covers enteral and/or parenteral applications.

In many embodiments, the feeding set has an inflow tubing line which connects to the container and an outflow tubing line which attaches to the patient. Between the inflow tubing line and the outflow tubing line is a piece of tubing which is more resilient and made according to more specific tolerances. This pump tubing segment engages the pump to deliver precise quantities of a desired fluid to the patient. The pump tubing segment is generally made of silicone and is more expensive, while the inflow tubing line and the outflow line can be made from less expensive tubing material which need not meet the more specific tolerances and performance characteristics of the pump tubing segment. Connectors are typically used to attach the pump tubing segment to the inflow tubing line and the outflow tubing line. The connectors may be disposed at opposing ends of a pump tubing segment for use in a linear or curvilinear peristaltic pump, or may be formed as one piece with the pump tubing segment being formed into a loop for engaging a rotor of a peristaltic pump. For ease of reference, both configurations may be referred to as a "cassette." Thus, as used herein, the cassette is the portion of the feeding set that engages the pump to control fluid flow.

One concern with feeding sets is controlling free flow situations. When a fluid is being infused into a patient, it is usually desirable for the rate of flow to be regulated. It is disadvantageous in many circumstances to have a condition, commonly referred to as free-flow, in which flow into the patient is controlled solely by the force of gravity. Such conditions can result in a large volume of solution being infused into a patient over a very short period of time. Due to medical conditions or medication contained in the infused solution, a free-flow condition can pose health concerns to a patient. In some situations it can even result in death of the patient.

Because of these concerns, numerous devices have been developed to regulate free-flow in medical pumps. One challenge with the use of anti-free-flow devices is retrofitting presently existing pumps. While newer pump models are typically designed to accommodate anti-free-flow devices, pumps that are already in existence may lack such structures. One concern with occluders used with some existing pumps is that a free-flow condition can occur if the infusion set is not properly mounted in the pump. For example, if the occluder is mounted in a mounting structure and moved into an open position to allow flow but the infusion set is not properly wrapped around the rotor of the pump, there is nothing to control the rate of flow through the infusion set.

One solution to prevent free flow in feeding sets is the use of an in-line occluder. In such devices, an occluder or stop is disposed inside the tubing of the infusion set, typically in the pump tubing segment. The stop prevents flow through the tubing unless a flow channel is formed between the tubing and the stop. In-line occluders are advantageous because they are relatively inexpensive and lower the risk of accidentally creating a free-flow condition.

One problem with in-line occluders is that many older enteral feeding pumps develop relatively low pumping pressures. Because of this, the pumping pressure is occasionally inadequate to overcome the occluder or requires sufficient force that the pump inaccurately determines that there is an undesired occlusion downstream from the pumping mechanism. This causes the generation of an alarm which requires the response of medical personnel to determine that the tubing is in fact not occluded. These nuisance alarms waste the time and effort of medical personnel and unnecessarily disrupt the infusion process.

For example, as shown in FIG. 1, a known occluder 1 is disposed in the tubing 2 of an infusion line and mounted in an existing pump 3 as generally done with pumps such as the pump 3. The tubing is held in tension at one end by a drip chamber 4 and by a connector 5 associated with the occluder 1 at the other end. Between the drip chamber 4 and the connector 5, the tubing is wrapped about a pump rotor 6 which engages the tubing to drive a solution through the tubing.

The occluder 1 is advantageous over many other occluders because it will prevent flow through the infusion tubing if the tubing is inadvertently removed from the pump rotor. Other occluders, such as some pinch clip or sliding occluders, are opened when the tubing 2 is mounted on the pump and will not close if the tubing becomes loose.

One issue with the occluder 1 configuration is nuisance occlusion alarms on older pump models. Many older pumps, such as the pump 3, have relatively low pumping power and will detect on undesired occlusion downstream based simply on the pressure needed to bypass the in-line occluder. Thus, it is desirable to have an occluder mechanism which will allow flow without nuisance alarms when the infusion set is properly mounted on the pump, and which will prevent a free-flow condition through the line if the tubing comes off the pump rotor or is otherwise not properly engaging the rotor.

While consideration has been given to simply opening the occluder when the infusion set is mounted on the pump, this still leaves open the risk of a free-flow situation. If the infusion line were inadvertently removed from around the rotor, the rotor would no longer act on the infusion line to control fluid flow. Thus, a free-flow situation could develop, potentially injuring the patient. Thus, there is a need for an apparatus and method for providing protection against a free-flow condition while avoiding nuisance alarms.

While in-line occluders and the like have made marked improvements in the control of free-flow situations, the prevalent use of peristaltic pumps in the medical industry has led to new inquiries seeking improved manufacturing techniques, lower costs, and easier use for care providers and consumers alike. Many attempts have been made to improve the state of the art of such technology, but room for improvement remains in the current technology. There are several areas for improvement associated with the use of peristaltic pumps and feeding sets.

One issue of concern is how to improve control of fluid flow when the feeding set is not mounted in and controlled by the pump. On one hand, it is disadvantageous to allow free-flow conditions. Likewise, it is disadvantageous to allow the solution to leak out of the feeding set. On the other hand, those loading the cassettes need to be able to allow flow through the feeding set to allow for priming of the cassette prior to use. While valves have been used to control fluid flow, they often make priming more difficult. In fact, some prior technology requires multiple hands to actuate a valve to prime the feeding set.

While the need remains to prevent free-flow and leakage in the feeding sets when not being used to deliver solutions under control of the pumping mechanism, there is also a need to establish, maintain, and increase ease-of-use and convenience for users and providers. Further, it is also desirable to meet these needs while reducing material and fabrication costs.

The technology improvements offered by the various aspects of the invention described herein enable new ways to meet improve usability and lower costs due to improved designs.

SUMMARY

An anti-free-flow mechanism for use with a medical pump and associated methods of use is disclosed. Embodiments of an anti-free-flow mechanism may include an occluder mechanism mounted on or in the infusion line which is biased into a closed position and which, when mounted on the pump, is opened as the infusion set is wrapped in tension around the rotor of the pump. The occluder mechanism may be configured to allow flow through the infusion tube as long as the tubing around the pump is in tension. In the event that tension is no longer present in the infusion pump around the tube, the occluder mechanism closes once again and prevents fluid from flowing through the tubing. Thus, flow through the tubing is not prevented as long as the tubing is properly mounted on the pump, but is terminated in the event that the tubing becomes loose.

According to some embodiments, the safety occluder is formed as a pinch clip which is biased so that the exterior of the tubing is pinched closed to prevent flow. Mounting the infusion set on the pump causes the pinching mechanism to be moved open. However, if the tubing is somehow removed from the rotor so that the infusion set is no longer in tension, the biasing element will return the pinching mechanism to an occluding orientation and thereby prevent fluid flow.

In other embodiments, a pinching mechanism is used to apply force to the tubing and thereby open a flow path past an in-line occluder when the infusion set is properly mounted in an infusion pump. However, when tension is released from the infusion set, the force on the tubing is released and flow through the infusion set is again stopped.

In accordance with another aspect of the present invention, an improved peristaltic delivery system is provided. Various aspects of the invention improve usability and/or lower cost for the delivery of fluids with a peristaltic pump. Thus, the various embodiments and aspects of the invention provide an improvement over the prior art.

In accordance with one aspect of the invention, a peristaltic pump system is contemplated. The pump system preferably includes a pump body having a mounting plate with a peristaltic pumping mechanism (e.g., a rotor) which is configured to receive and removably capture a cassette of a feeding set. The cassette may include a pump tubing segment disposed to engage the pumping mechanism, and a valve formed by the pump tubing segment and an inline occluder to form a valve which selectively prevents flow through the lumen in the tubing.

The cassette may include a deflectable primer or actuator formed with an actuation pad disposed adjacent the pump tubing segment and occluder. The primer has a first position wherein it is disposed away from the tubing segment and occluder such that the tubing segment and occluder form a valve which is in a biased closed orientation, and a second position wherein the actuator is moved into contact with the tubing segment to distend or deform the tubing segment adjacent the occluder and open a flow channel between the occluder and the tubing segment.

In accordance with one aspect of the invention, the actuator may have a pad configured to deform the pump tubing segment adjacent the occluder to open flow in the lumen past the occluder, thereby opening the valve to allow flow through the feeding set. In some embodiments, the pad may have an tapering channel which engages the tubing segment to stretch or deform the pump tubing segment adjacent the occluder.

In accordance with another aspect of the invention, the actuator and occluder may be positioned on the cassette adjacent the inflow line or the outflow line to enable priming of the lumen from a location upstream or downstream from where the pumping mechanism will engage the cassette.

In accordance with another aspect of the invention, the actuator may include a flex joint integrally formed with the carrier or connector and extending therefrom. A flexible or bendable arm may also extend from the flex joint to an extent proximate the location of the occluder in the tubing segment.

In accordance with still yet another aspect of the invention, the actuator may have an engagement member which may include projections forming a channel which includes a radius similar to that of the tubing wall which defines the lumen, or similar to the outer diameter of the occluder stop.

In accordance with another aspect of the invention, the actuator may include one or more load distributors along the arm.

In accordance with another aspect of the invention, at least one reinforcement may also be incorporated about the actuator either alone or in combination with any of the configurations described herein. The at least one reinforcement may be included about the flex joint and/or flexure arm to establish a pre-established and or predetermined preload to the actuator so that a predetermined amount of force must be imparted to deflect the actuator into engagement with the tubing segment adjacent the occluder.

In yet another aspect of the invention, the flex joint, the arm, and the at least one flexure reinforcement may be employed alone or in combination and may form the entire actuator, or may be incorporated as a part of the actuator.

In accordance with yet another aspect of the invention any of the embodiments of the innovative fluid delivery sets may also include an actuator arm that can depend or extend from the carrier or connector to an extent of the actuator.

In accordance with another aspect of the invention, an engagement member (which may also be referred to as an actuation pad or deformation anvil) may be carried on the actuator and may be urged against the tubing segment proximate the inline valve formed by the occluder and tubing segment. When so deflected and urged, the engagement member engages and deforms a portion of the tubing segment to form one or more flow channels between the tubing segment and the occluder.

In accordance with yet another aspect of the invention, the mounting plate of the pump and/or the cassette may include one or more walls or elements that can capture the cassette on the mounting plate when the pump tubing segment is placed in tension on the mounting plate. The walls or elements may include complementary surfaces and/or recesses and projections to hold the cassette in place on the mounting plate. Additionally, the recesses and projections may be configured to provide a human perceptible signal to verify that the cassette has been properly mounted on the mounting plate.

In yet another aspect of the invention, the cassette body and the pump mounting structure each have complementary engagement members which have complementary engagement surfaces. The engagement members are configured so that the engagement surfaces will suddenly align as the engagement surfaces slide with respect to one another, thereby providing a sound or other human perceptible signal that the engagement surfaces of the cassette body and the mounting structure are properly aligned and that the cassette body is properly held in place on the pump.

The various aspects of the invention may be made and used either alone or in combination with one another and with the features and elements already known in the prior art. Such embodiments can be better understood by those with relevant skills in the art with reference to the following detailed description of the preferred embodiments and the accompanying figures and drawings.

BRIEF DESCRIPTION OF THE DRAWINGS

Various embodiments are shown and described in reference to the numbered drawings wherein:

FIG. 2A shows a plan view of an exemplary occluder mechanism according to embodiments of the invention and a mounting structure configured for receiving the occluder mechanism;

FIG. 2B shows a close-up view of the actuator and slide shown in FIG. 2A;

FIG. 2C shows a view of the occluder mechanism of FIG. 2A disposed in the mounting structure;

FIG. 9A shows a perspective view of and exemplary embodiment of yet another occluder mechanism;

FIG. 9B shows an end view of the occluder of FIG. 9A;

FIG. 9C shows a side cross-sectional view of the occluder of FIGS. 9A and 9B taken along line A-A;

FIG. 10A shows a perspective view of yet another occluder mechanism along with infusion tubing.

FIG. 10B shows the occluder mechanism of FIG. 10A with the infusion tubing removed to show the in-line occluder;

FIG. 10C shows an end view of the occluder mechanism of FIG. 10A;

FIG. 33 shows a close-up, cross-sectional view of the engagement surfaces of a cassette body and pump body in accordance with another embodiment of the present invention;

FIG. 34 shows a close-up view of the engagement members of FIG. 26 with the engagement surfaces separated from one other;

It will be appreciated that the drawings are illustrative and not limiting of the scope of the invention which is defined by the appended claims. The various elements in the illustrated embodiments are exemplary and not comprehensive of all possible variations and embodiments. It is appreciated that not every element can be clearly displayed in a single drawing, and as such every drawing may not show each and every element of each embodiment.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims.

Turning now to FIG. 2A, a cut-away view of an occluder mechanism 10 is illustrated, which is configured for placement along a segment of tubing 14 of an infusion or feeding set.

Figure 1:
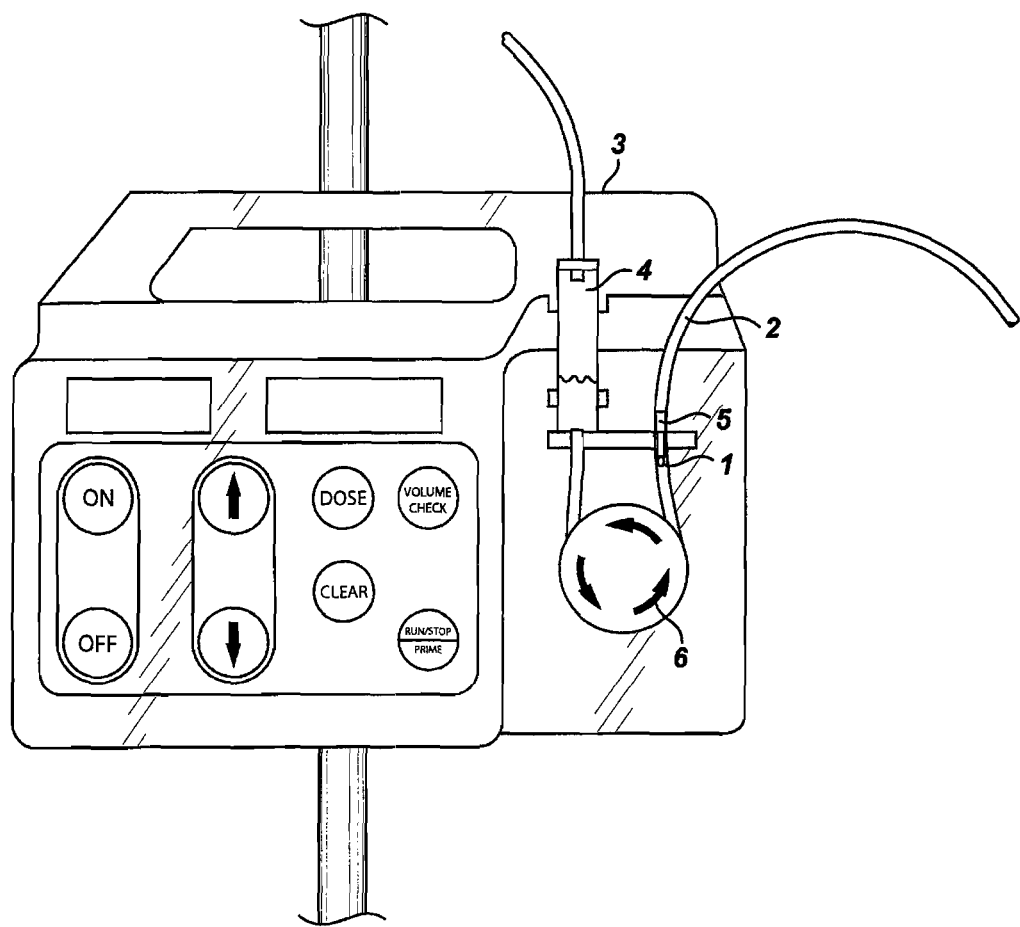
FIG. 1 shows a common enteral feeding pump having an in-line occluder disposed therein in accordance with the prior art.

FIG. 2A also shows a cross-sectional view of a mounting structure, generally indicated at 20 for use on a medical pump, such as the enteral feeding pump shown in FIG. 1. (As will be explained in additional detail below, the mounting structure 20 may be an adaptor which is a separate piece from the pump itself, or it can be the mounting structure on the pump which is traditionally used to load an infusion set.)

The occluder mechanism 10 may include a plunger or slider 24 which engages the tubing 14. A biasing element 28, such as a spring, band, etc., may bias the slider 24 into engagement with the tubing 14 so as to pinch the tubing closed and thereby occlude the tube and prevent flow therethrough. Thus, the occluder mechanism 10 may be biased in a closed position which prevents flow.

An actuator 32, typically in the form of a pivot clip, may be disposed in engagement with the slider 24. Movement of the actuator 32, e.g. rotation of the pivot clip about an axis 34 (FIG. 2B), moves the slider 24 against the bias of the biasing element 28, and causes the slider to no longer pinch the tubing in a closed position. Thus, movement of the actuator 32 allows flow through the tubing 14.

The occluder mechanism 10 has at least one sloped sidewall 36 which is configured to allow the occluder mechanism to nest in the mounting structure 20 so that the sloped sidewall 36 engages a sloped sidewall 40 of the mounting structure 20 or some other structure in the sidewall. As the tapered occluder mechanism 10 slides into the tapered opening in the mounting structure 20, the wall 40 helps to center the occluder mechanism.

The wall 40 or a portion thereof may also engage the actuator 32 and push it inwardly into the occluder mechanism 10. This causes the slider 24 to move out of the closed, pinching position and into an open, non-occluding position where flow through the tubing 14 is enabled. Thus, mounting the occluder mechanism 10 in the mounting structure 20 opens flow through the tubing, as shown in FIG. 2C. (While the actuator 32 is shown as being generally L-shaped, it may be triangular or a number of other shapes in cross-section to facilitate pivoting and movement of the slider 24).

The engagement of actuator 32 and the sidewall 40 of the mounting structure 20, however, prevents the occluder mechanism 10 from remaining in the mounting structure in the event that the tubing 14 is not properly loaded. The biasing element 28 provides a force against the slider 24, and thus against inward movement of the actuator 32. If an external force is not applied to the occluder mechanism 10, the biasing element 28 will cause the occluder mechanism (via the slider 24 and actuator 32) to push against the mounting structure 20 to move upwardly, thereby returning the slider 24 into the occluding position. To overcome this biasing, the tubing 14 is placed in tension when it is wrapped around the rotor of the pump as represented by the arrow 50 in FIG. 2C. (In other pump configurations, the tension on the tubing may be created by a mounting structure mounting in the pump or by use of a drip chamber, which is spaced sufficiently away from the occluder mechanism 10 and mounting structure 20, that the tubing 14 is placed in tension when properly mounted in the pump).

If the tension on the tubing 14 is relieved, i.e., if the tubing inadvertently comes off the pump rotor, the downward pull on the tubing represented by arrow 50 disappears and the bias of the biasing element 28 on the slider 24 and actuator 32 overcomes the effect of gravity on the occluder mechanism 10 and the pushes the occluder mechanism 10 upwardly in the mounting structure 20. This returns the actuator 32 to its original position and allows the slider 24 to occlude flow. It will be appreciated that the actuator 32 need not return the occluder mechanism 10 to the top of the mounting structure. Rather, the actuator 32 need only push the occluder mechanism upwardly sufficiently for the slider 24 to occlude flow through the tubing. This can be assisted by a void 48 in the sidewall 40 of the mounting structure 20.

It will be appreciated that the mounting structure 20 may be mounted on any number of different pumps in a variety of ways. Some pumps, such as that shown in FIG. 1, already include a structure downstream from the pump rotor on which the mounting structure 20 can be mounted. Other pumps may require the mounting structure to be adhesively or otherwise attached. Such attachments will be apparent to those of skill in the art and are not discussed herein in detail.

Figure 3A:
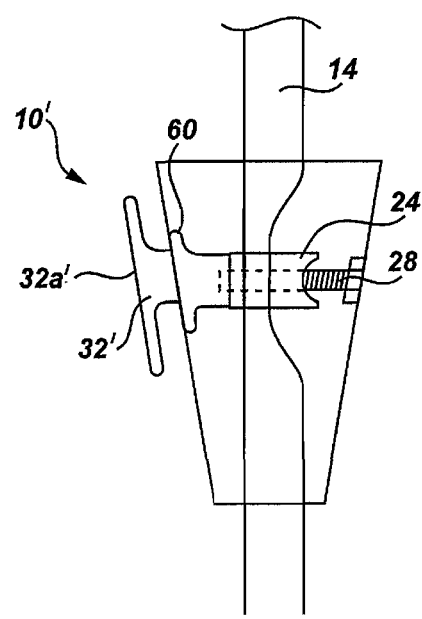
FIG. 3A shows a cross-sectional view of an exemplary occluder mechanism and mounting structure.
Figure 3A:
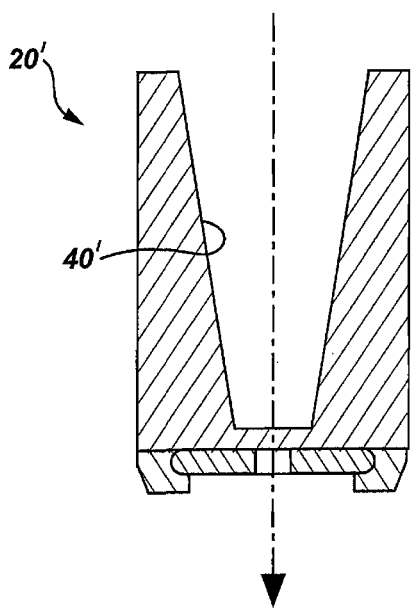
Figure 3B:
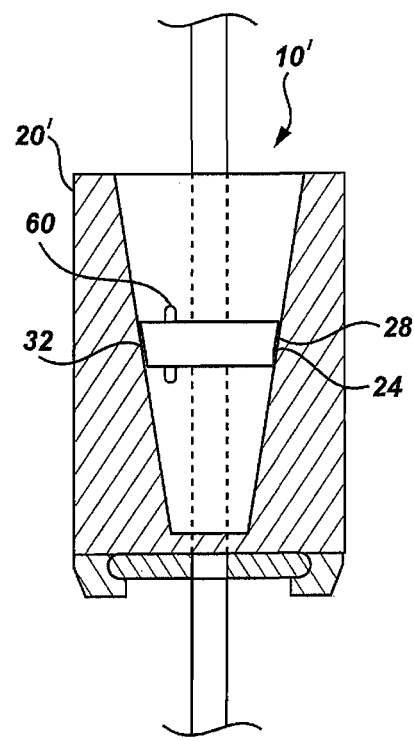
FIG. 3B shows the occluder mechanism of FIG. 3A mounted in the housing so as to allow flow through the infusion tubing.

Turning now to FIGS. 3A and 3B, there is shown an alternate configuration of an occluder mechanism 10' and a mounting structure 20'. The occluder mechanism 10' is mounted on a segment of tubing 14 of an infusion set. Like the occluder mechanism 10 of FIGS. 2A-2C, the occluder mechanism 10' includes a slider 24 which is biased by a biasing element 28 into a closed or occluding position where the slider 24 pinches closed the tubing 14. Rather than a pivoting actuator 32 in FIGS. 2A-2C, the occluder mechanism 10' in FIGS. 3A-3B has an actuator 32' which moves linearly to move the slider 24 out of the first, closed or occluding position and into a second, open or non-occluding position.

The mounting structure 20' includes a sloped wall 40' which interacts with a sloped wall 32a' on the actuator 32'. As the occluder mechanism 10' is drawn down into the mounting structure 20', the wall 32a' interacts with wall 40' and pushes against the biasing element 28 to move the slider 24 into the open position. Due to the force of the biasing element 28, however, a downward force must be placed on the occluder mechanism 10' to overcome the bias. This is done by the tension on the tubing 14. If the tension is released, the biasing element 28 will push against the slider 24, which will force the actuator 32 outwardly. The sloped interaction between the mounting structure 20' and the wall 32a' of the actuator 32 will cause the occluder mechanism 10' to rise sufficiently that tubing 14 is pinched closed by the slider 24'.

It will be appreciated that the housing 12 of the occluder mechanism 10 or 10' need not be sloped. Likewise, the entire wall 40, 40' need not be sloped. Rather, only portions may be needed on the mounting structure 20 or 20' and the actuator 32 or 32', which interact to allow for conversion of the force of the biasing element 28 into movement of the occluder mechanism 10, 10' when the tubing 14' is not in tension.

FIGS. 3A and 3B also show a stop 60 disposed on the slider 24. The stop 60 is disposed to prevent the slider 24 from coming out of the occluder mechanism 10' if the tubing is not present. It also prevents the slider 24 from overly pinching the tube when the occluder mechanism 10' is not disposed in the mounting structure 20'.

It will be appreciated that the interior of the occluder mechanism 10 or 10' may include a wall disposed on one side of the tubing 14 to aid the slider 24 to pinch closed the tubing. In other words, one side of the tubing 14 is held by the wall and the opposing side is engaged by the slider 24 to pinch the tubing closed.

Figure 4A:
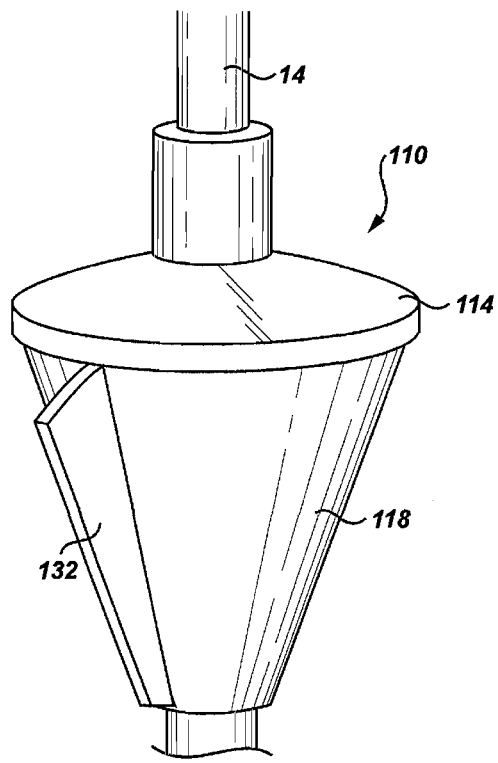
FIG. 4A shows a perspective view of an exemplary embodiment of an occluder mechanism.
Figure 4C:
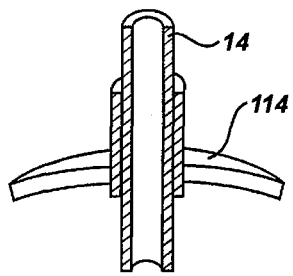
FIG. 4C shows a cross-sectional view of the top of the occluder mechanism of FIG. 4A and a portion of tubing.

Turning now to FIG. 4A, embodiments of an occluder mechanism 110 are illustrated. The occluder mechanism 110 includes a top 114 and a base 118. As shown in FIG. 4C, the top 114 can be used to secure the occluder mechanism 110 into a segment of tubing 14 of an infusion set. This can be accomplished by a variety of mechanisms, including using an adhesive.

The occluder mechanism 110 also includes a base 118. The base 118 may be configured to nest in a mounting structure, such as mounting structure 20' in FIGS. 3A and 3B. However, it will be appreciated that other configurations can be used for the mounting structure while still accomplishing the selective termination of fluid flow through the tubing 14 as described herein.

The base 118 may include an actuator 132 which pivotably extends from the base. As shown in FIG. 4B, the actuator 132 is attached to a plunger or slide 124 which engages the tubing 14 to selectively terminate flow. The slide 124 is biased into a first, closed position by a biasing element 128, such as a spring. When no other force is acting on the slide 124, the slide is forced into the side of the tubing 14, thereby pinching the tubing closed. When in this state, the actuator 132 will extend from the side of the base 118 as shown in FIG. 4A. However, application of a force to the actuator 132 to move it into the position shown in FIG. 4B, moves the slide 124 against the bias of the biasing element 128 and away from the tubing 14, thereby allowing flow through the tubing.

Because of the slope presented by the far end of the actuator 132 when it is extended, extending the actuator will tend to lift the base out of the mounting structure (e.g. mounting structure 20' in FIG. 3A). As the base 118 is lifted, the actuator 132 is able to continue to move outwardly and the slide 124 forcefully engages the tubing. Thus, unless the base 118 is secured in the mounting structure 20', etc., the biasing element 128 will cause the slide 124 to pinch closed the occluder. The base 118 is secured in the mounting structure by having the tubing 14 be in tension in a direction which will hold the occluder mechanism 110 in place.

Such a configuration may be highly advantageous in the context of a medical pump. If the infusion set is not properly loaded, the occluder mechanism 110 will remain with the plunger or slider 124 in the first, occluding position, thereby preventing a free-flow situation which could cause injury to the patient. Once the infusion set is properly loaded, the occluder mechanism 110 is moved into the second, open position where it will not interfere with the pump's operation and will be less susceptible to causing false occlusion alarms. In the event the tubing 14 is accidentally removed from proper placement on the pump (e.g., the tubing is inadvertently pulled off the rotor), the occluder mechanism is lifted or otherwise moved sufficiently to enable it to return to the occluding position. Thus, free-flow is avoided even when the tubing 14 is inadvertently removed from its proper position.

Figure 4D:
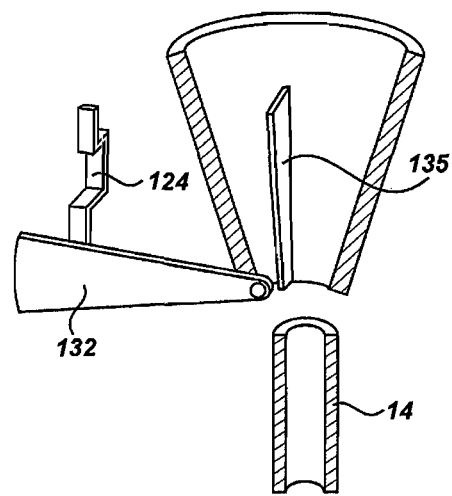
FIG. 4D shows a cross-sectional view of the base portion of the occluder mechanism of FIG. 4A, with the occluder extended for visibility.
Figure 4B:
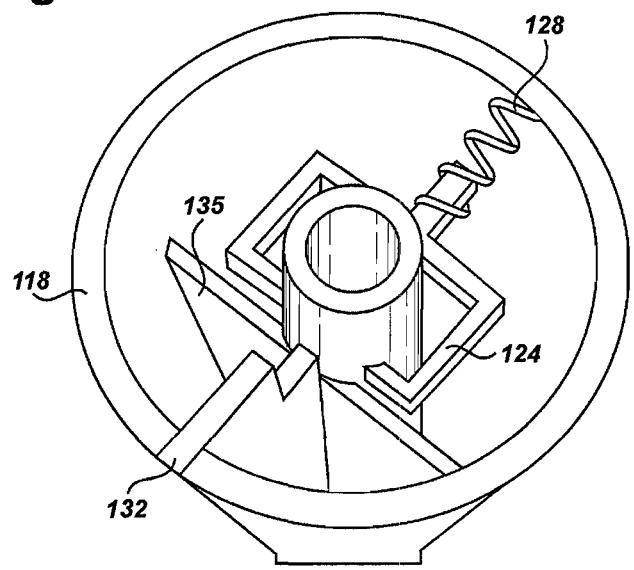
FIG. 4B shows a top view of the base of the occluder mechanism of FIG. 4A with the top removed to show the occluder acting on a portion of tubing of the infusion set.

FIG. 4D shows a cross-sectional view of the base 118 with the actuator 132 and slider 124 pivoted out of the way to show a wall 135. The wall 135 helps secure the tubing 14 so that it can be pinched closed by the slide 124.

Figure 4E:
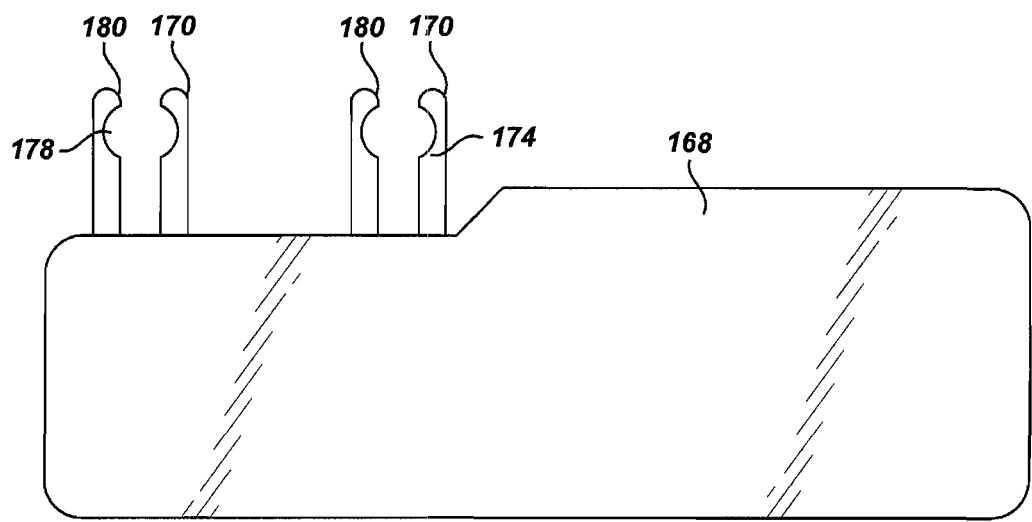
FIG. 4E shows a top view of a pump and the mounting structure which is used to secure the infusion set to the pump.

FIG. 4E shows a top view of a pump 168 similar to that shown in FIG. 1. While the mounting structure of the present invention may be an adapter for attachment on a pump, such as those shown regarding FIGS. 2A-3B, the mounting structure may also be the conventional mounting structure on a pump. For example, the COMPAT pump made by NESTLE uses two sets of mounts 170. One mount 174 is used to receive a drip chamber, while the other mount 178 is used to hold other structures, such as an adaptor for connecting a tubing segment which is worked by the pump rotor (not shown) to a longer, less expensive piece of tubing which connects to the patient via a stoma catheter, etc.

The mounts 174 and 178 include a receiving portion 180 which is tapered or generally frusto-conical (excepting the openings). The receiving portions can receive the occluder mechanism 10, 10' etc. and facilitate lifting of the occluder mechanism if tension is not maintained on the tubing. It will be appreciated that other pumps may have receiving portions which are not tapered. However, the actuator 32 or 32' can be configured to still engage the receiving portion and lift the occluder mechanism to thereby occlude flow.

Figure 5:
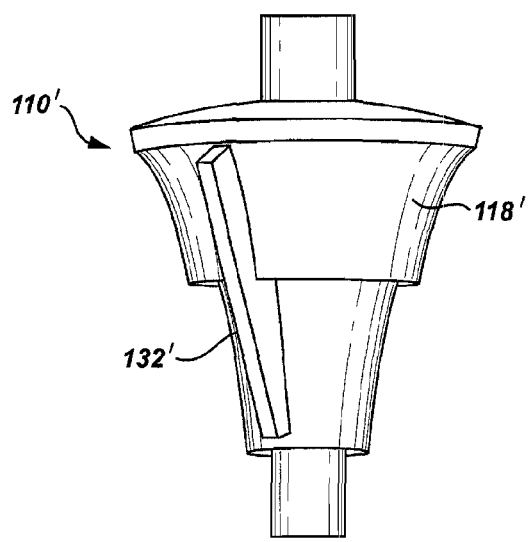
FIG. 5 shows a perspective view of an exemplary embodiment of an occluder mechanism.
Figure 6:
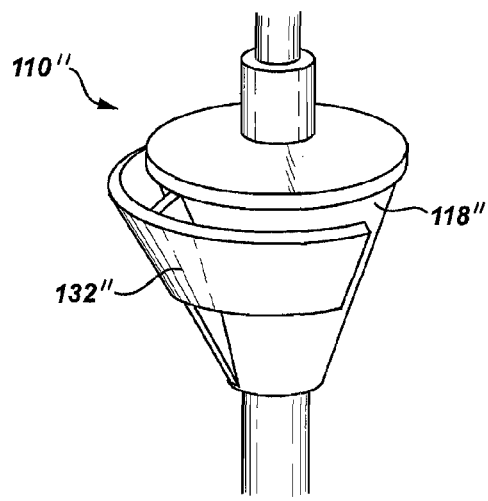
FIG. 6 shows a perspective view of an exemplary embodiment of an occluder mechanism.
Figure 7:
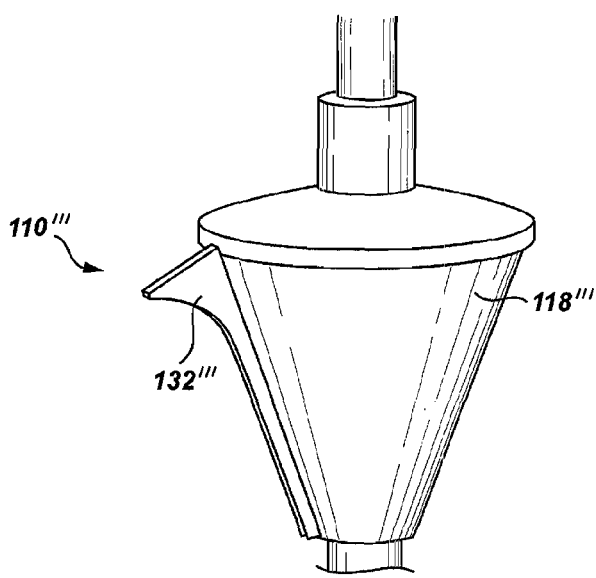
FIG. 7 shows a perspective view of yet another exemplary embodiment of an occluder mechanism.

FIG. 5, FIG. 6 and FIG. 7 each show a perspective view of embodiments of occluder mechanisms 110', 110" and 110''' having different bases 118', 118" and 118''' and/or various configurations of the actuator 132', 132" and 132'''. The base and actuator can be configured so as to require a specific configuration of a mounting structure, or can be configured to allow a single occluder mechanism to be used with multiple pumps. For example, the base 118' is stepped so that it may be inserted into pumps having a different sized receiving portion on the mounting structure. The actuator 132" may be used to prevent the occluder mechanism 110" from being inserted into the mounting structure designed for occluder mechanism 110'''.

Figure 8B:
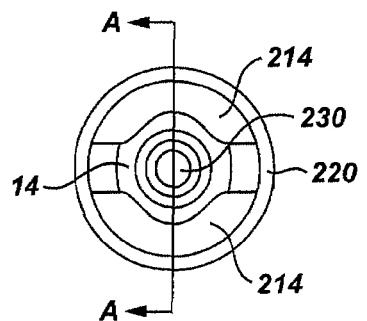
FIG. 8B shows an end view of the occluder mechanism of FIG. 8A.
Figure 8D:
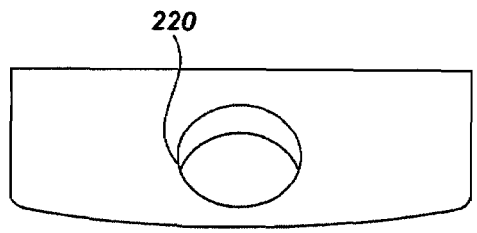
FIG. 8D shows a mounting structure for receiving the occluder mechanism shown in FIGS. 8A-8C.
Figure 8A:
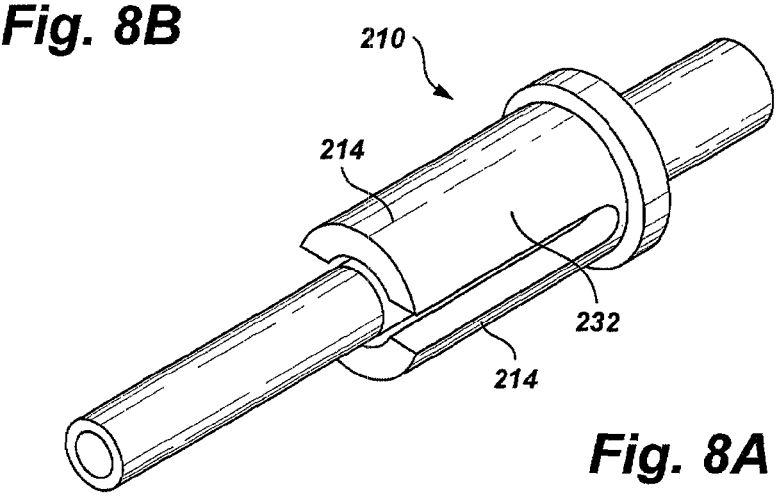
FIG. 8A shows a perspective view of still another configuration of an occluder mechanism.
Figure 8C:
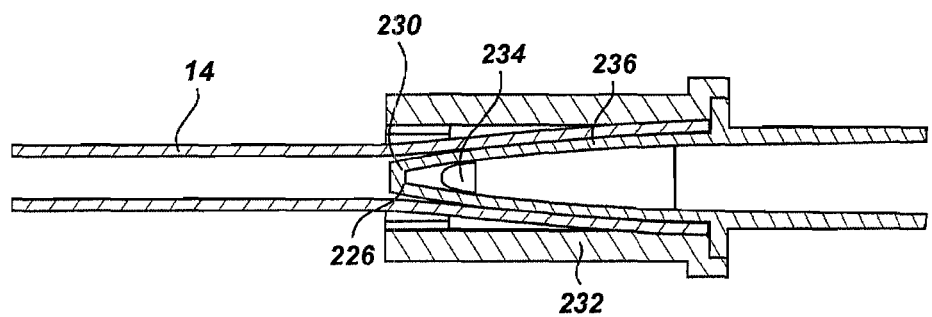
FIG. 8C shows a side cross-sectional view taken along line A-A in FIG. 8B.

Turning now to FIGS. 8A through 8D, there is shown an embodiment of an occluder mechanism that involves the use of an in-line occluder—i.e. an occluder which occludes flow by disposition inside of the tube, rather than by pinching the tubing closed. Referring specifically to FIG. 8C, there is shown a cross-sectional view of tubing 14 of an infusion set with an occluder 226 disposed inside the tubing. The occluder 226 includes a stop 230 which typically has an outer diameter which is slightly larger than the inner diameter of the tubing. The stop 230 prevents fluid flow through the tubing unless a flow channel is opened past the stop. (A more detailed description of such occluders is set forth in U.S. Pat. No. 7,150,727, which is incorporated herein by reference.) When a flow channel is open, the fluid flows past the stop 230 and into an opening 234 in a body 236 which can also serve as a connector for attaching segments of an infusion line. Once past the stop 230, the fluid is free to travel downstream through the channel in the body and through the remainder of the infusion set.

Opening a flow channel past the stop 230 can be accomplished in several ways. One common method is to simply provide sufficient pressure to radially expand the tubing 14 so that a flow path opens around the tubing. As mentioned in the background section, however, this method can create false alarms suggestion that the tubing is occluded downstream.

Another method to open a flow channel may be to apply force to the tubing adjacent the stop 230. When force is applied, the tubing tends to deform and open a flow channel around the stop 230. By controlling where the force is applied to the stop, the configuration of the openings can also be controlled as discussed in the '727 patent. Applying force on one side can create a single channel, while applying force on opposing sides will create a flow channel on each side perpendicular to the application of force.

In FIG. 8A, the occluder mechanism 210 may include a body forming an actuator 232 in the form of a pair of arms 214. The arms 214 are bendable or pivotable to engage the stop 230 when they are mounted in a mounting structure 220 (FIG. 8D or 170 in FIG. 4E) to open fluid flow past the stop.

While it operates with an in-line occluder rather than a pinch occluder, the occluder mechanism 210 can function similarly to those discussed above in that when the occluder mechanism 210 is disposed in the mounting structure 170 or 220 and tension is applied, the tubing is opened for fluid flow controlled by the pump. If, however, tension is not present on the tubing, the biasing of the arms 214 (like the biasing element 128) will allow the tubing to be returned to an occluded orientation. Alternatively, the occluder mechanism 210 can be configured so it nests in the mounting structure 170, 220 and remains open regardless of tension on the tubing—thereby forgoing automatic closure if the tubing 14 is not loaded properly. Whether the occluder mechanism 210 provides automatic closure will depend on the engagement between the occluder mechanism and the mounting structure.

If medical personnel need to temporarily open the occluder mechanism 10, 10', 110, 110', 110", 110''' or 210, he or she need only apply force to the actuator 32, 32', 132, 132', 132", 132''' or 232 to open flow through the tubing. As soon as the pressure is released, however, the flow past the occluder is terminated. Thus, the risk that medical personnel accidentally leave the tubing in a free-flow state is eliminated.

Turning now to FIG. 9A, there is shown an occluder mechanism 210' which is a variation of the occluder mechanism 210 of FIG. 8A. Rather than using a pair of arms 214 as the actuator 232 in the occluder mechanism of FIG. 8A, a single arm 214' acts as the actuator 232' and pivots into forceful contact with the tubing adjacent the stop 230 to open a flow channel past the stop. Additionally, as shown in FIG. 9C, the ends 214a of the arm 214' may have relatively sharp corners at the front and rear to engage the tubing 14 while the curved walls of the channel are angled to engage the tubing segment and distend the tubing segment to help open the flow channel. One advantage of the configurations shown in FIGS. 8A through 9C is that they can be used with in-line occluders already in use with pumps such as that shown in FIG. 1, thus minimizing retooling.

It will be appreciated in light of the disclosure that the body of the occluder which forms the actuator 214, 214' and the body 236 of the occluder which extends from the stop may be a single body or may be attached to one another in a variety of methods including snap-fit, pressure fit, bonding or other adhesives, etc.

Figure 10D:
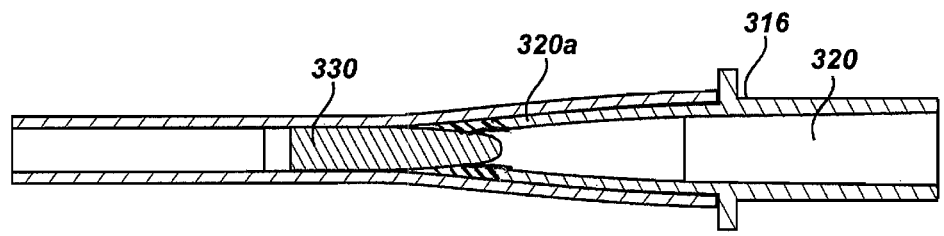
FIG. 10D shows a side cross-sectional view of the occluder mechanism of FIG. 10A with the in-line occluder in a closed configuration.

Turning now to FIGS. 10A-10E, there are shown various views of yet another occluder mechanism, generally indicated at 310, formed in accordance with principles of the present invention. The occluder mechanism 310 includes a connector 316 having a channel 320 extending therethrough. A stop 330 is disposed in a segment of an infusion set tubing 14 which attaches to the connector. FIG. 10B shows a perspective view of the stop 330 and the connector 316 with the tubing removed and which the stop 330 is disposed in a first, closed or occluding position.

The stop 330 has a plurality of projections 336 which are spaced apart to leave channels 340. The ends of the projections 336 are configured to remain in contact with the tubing 14, while the channels 340 allow fluid to flow along the stop for the distance for which the projections engage the tubing.

FIG. 10D shows a side cross-sectional view of the stop 330 and connector 316 taken along lines A-A in FIG. 10C with the stop in a closed position. Downstream from the channels 340, the stop 330 is configured to seat in the opening to the channel 320 in the connector 316. Because the tubing 14 is usually elastomeric, the stop 330 can be placed in the tubing so that a small amount of force is applied to maintain the stop 330 seated in the opening 320a in the connector. In other words, the stop 330 is biased into a closed or occluding position. In this position, flow will not occur through the connector. Thus, the stop 330 remains in a first, closed or occluding position unless acted on by some external force.

Figure 10E:
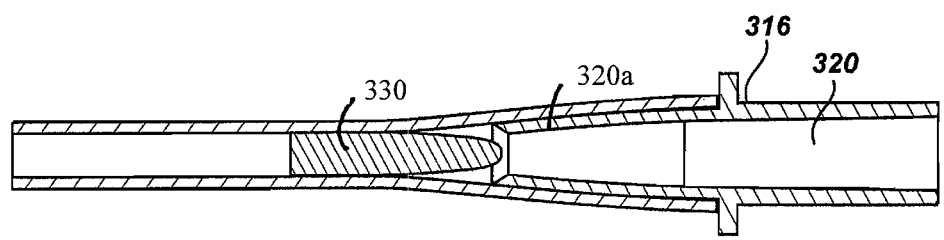
FIG. 10E shows a side cross-sectional view of the occluder mechanism of FIG. 10A with the in-line occluder in an open configuration.

When the tubing 14 is placed in tension by mounting on a pump, a portion of the tubing 14 distal from the connector 316 is pulled away from the connector. The elastomeric tubing will stretch and the stop 330 is pulled at least partially out of the connector 316 as shown in FIG. 10E. The projections 336 and channels 340 prevent the tubing from collapsing on the stop 330 sufficiently to prevent flow past the stop. Thus, the stop 330 is moved into a second, open or non-occluding position. As soon as the tension on the tubing is released, however, the stop 330 will be drawn back into the connector 316, thereby precluding flow.

Figure 11A:
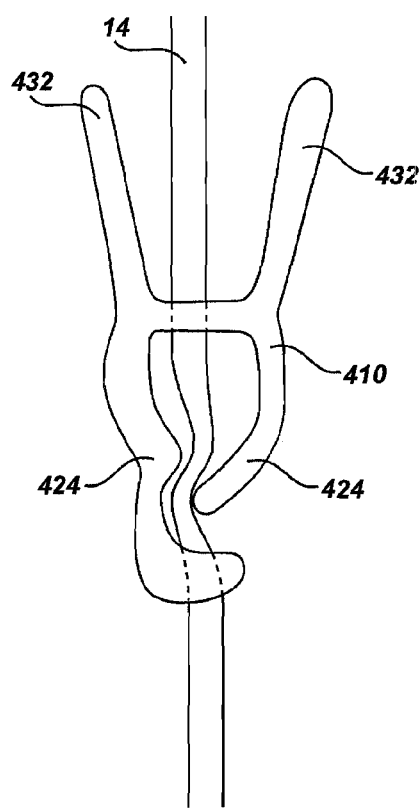
FIGS. 11A and 11B show yet another occluder mechanism and mounting structure for selectively preventing free-flow in an infusion set.

Turning now to FIG. 11A, there is shown a pinch clip occluder 410 mounted on a segment of infusion set tubing 14. The pinch clip occluder includes a pair of arms 424 which are biased to pinch closed the tubing 14. A pair of flanges 432 extends outwardly from the arms 424 such that pinching the flanges 432 draws the arms away from each other, thereby opening flow through the tubing 14.

Figure 11B:
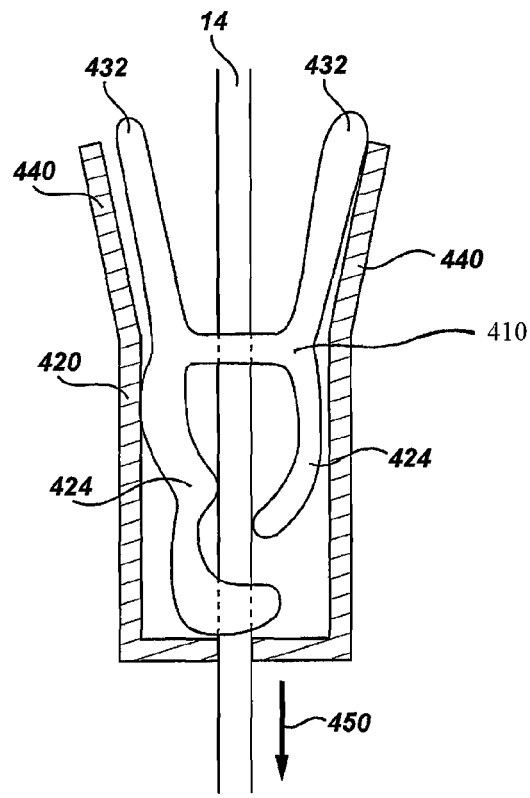

FIG. 11B shows the pinch clip occluder 410 mounted in a mounting structure 420. The mounting structure 420 has a pair of sloped walls 440 which engage the flanges 432 and push them toward one another to thereby pull apart the arms 424 and thereby open flow through the tubing 14. The slope of the wall 440, however, allows the natural bias of the flanges to urge the pinch clip occluder 410 out partially out of the housing 420. Thus, unless a force is applied by tension on the tubing, as represented by arrow 450, the flanges 432 will return to their original position and occlude flow through the tubing.

Figure 12A:
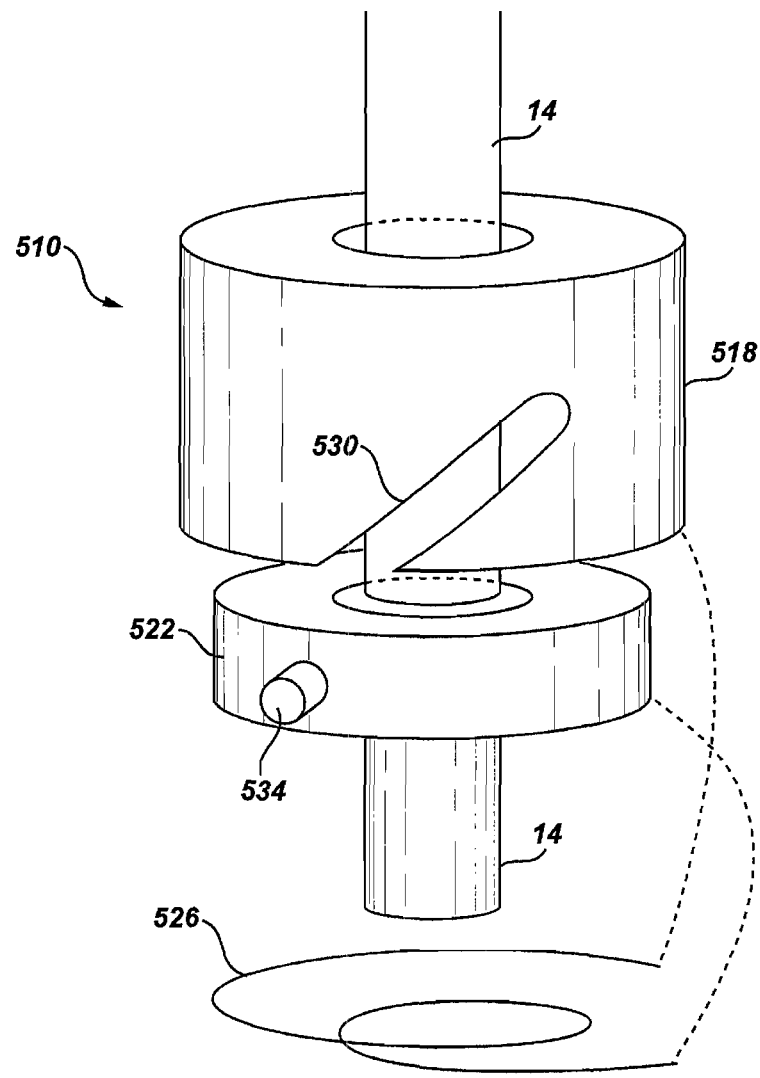
FIG. 12A shows an exploded view of yet another occluder mechanism.

FIG. 12A shows an exploded view of yet another occluder, generally indicated at 510, disposed along a segment of tubing 14 of an infusion set. Rather than using a plunger or slide, or an in-line occluder as the previous occluders, the occluder 510 includes a first body 518 and a second body 522, each of which is attached to the tubing 14. The first body 518 is also attached to the second body 522 by a torsional spring 526.

Figure 12B:
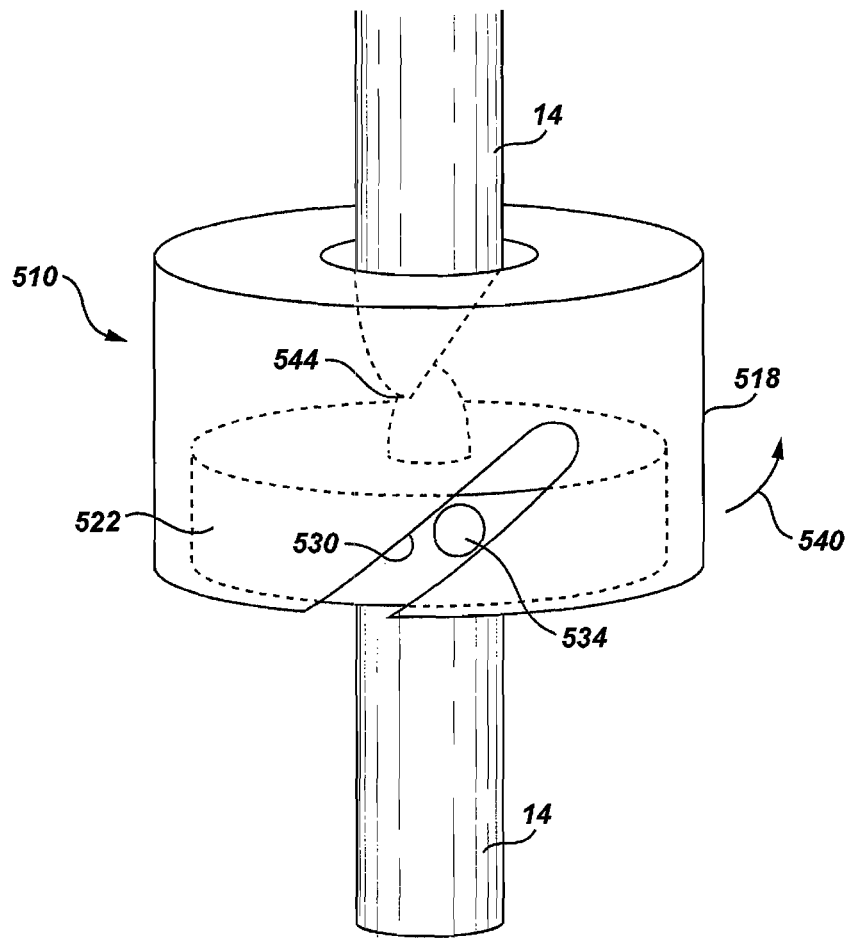
FIG. 12B shows the occluder mechanism of FIG. 12A, with the occluder in a closed, occluding position.

The first body 518 also includes a channel 530 configured for receiving a projection 534 on the second body 522. The second body 522 is configured to nest in and travel helically in the first body 518 under a bias from the by the torsional spring 526. As the second body 522 moves upwardly, the projection 534 travels in the channel 530, causing the second body to rotate as shown by arrow 540 in FIG. 12B. Rotating the second body 522 also rotates that portion of the tubing 14 to which it is attached. The first body 518 and the portion of tubing to which it is attached, do not rotate however. Thus, as the second body 522 moves, the tubing 14 is twisted closed, (shown at 544 in FIG. 12B) thereby preventing free-flow through the tubing.

When the tubing 14 is mounted in a pump under tension, the downward force on the tubing 14 pulls against the bias of the torsional spring 526 (FIG. 12A). This pulls the second body 522 downwardly in the first body 518 and causes rotation of the second body due to the interaction of the channel 530 and projection 534. This rotation returns the tubing 14 to its normal, untwisted configuration and opens flow through the tubing 14. If tension on the tubing 14 is released, however, the torsional spring 526 will lift and turn the second body 522, thereby occluding flow through the tubing.

It will be appreciated that the various types of fluid control devices contained herein can be used with a variety of types of peristaltic pumps. Such pumps may include linear, curvilinear and rotary peristaltic pumps. Additionally, each may be incorporated into cassettes which have additional features.

Figure 13:
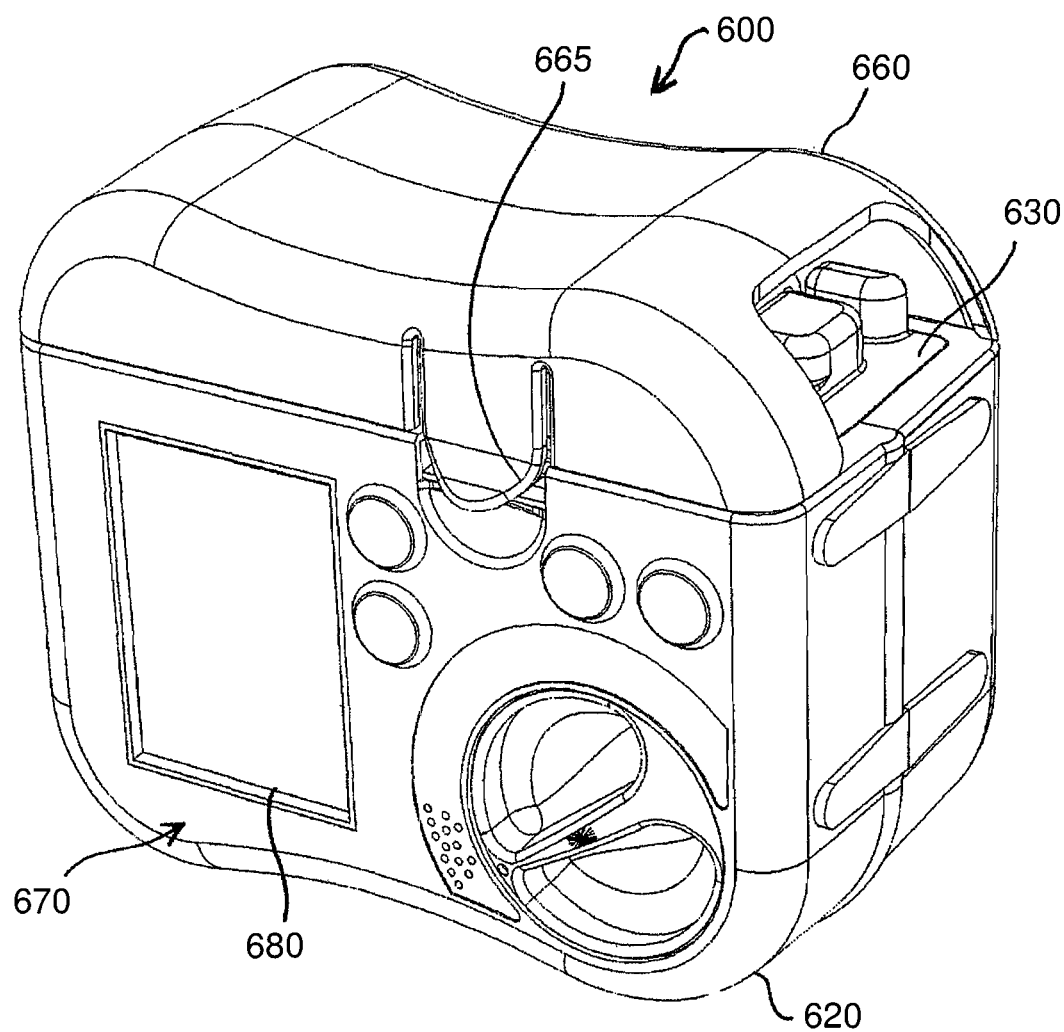
FIG. 13 is an elevated perspective view of a peristaltic pump delivery system according to the principles of the invention.
Figure 14:
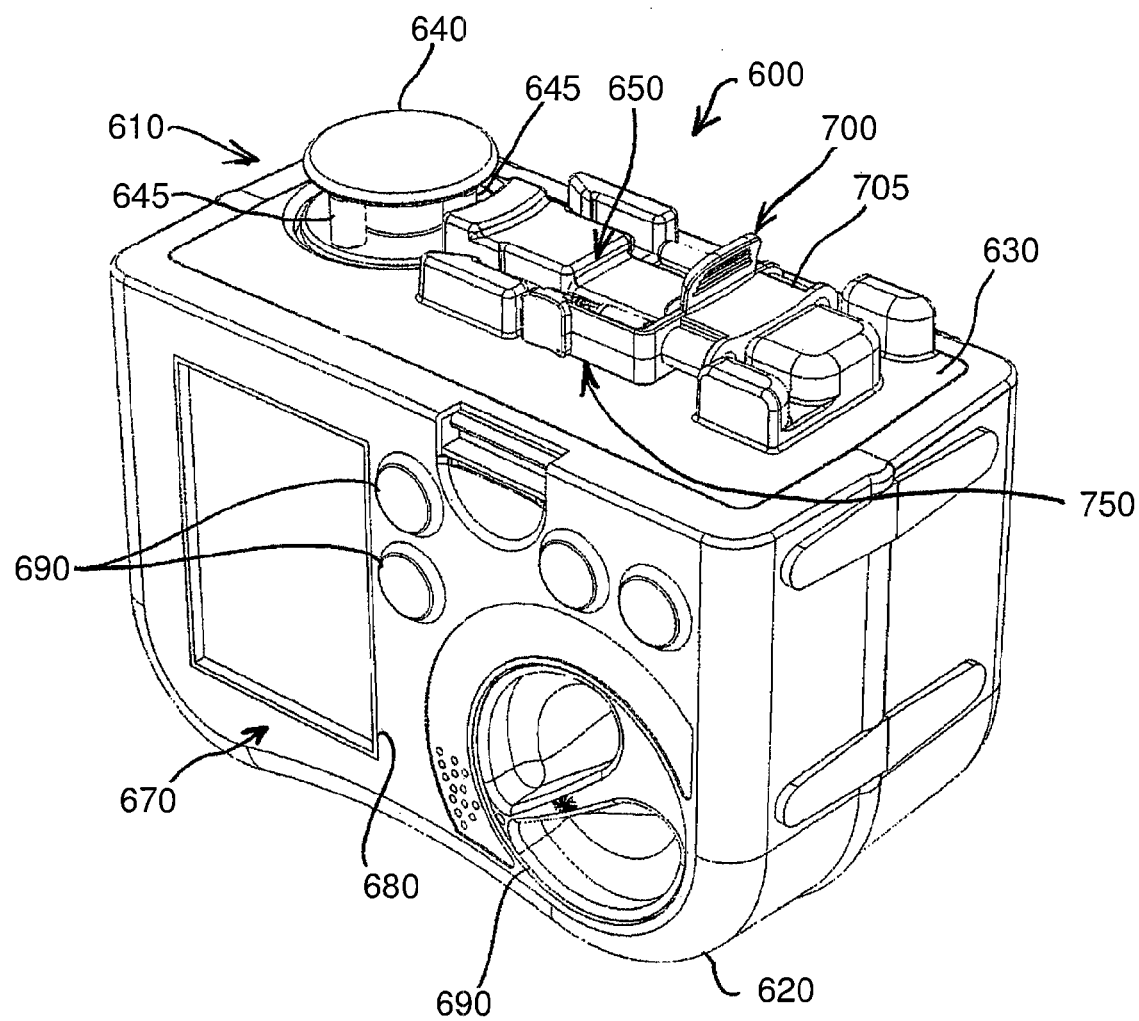
FIG. 14 is another perspective view of the system of FIG. 13 with the door removed to show the mounting plate of the pump with a cassette body mounted thereon.
Figure 15:
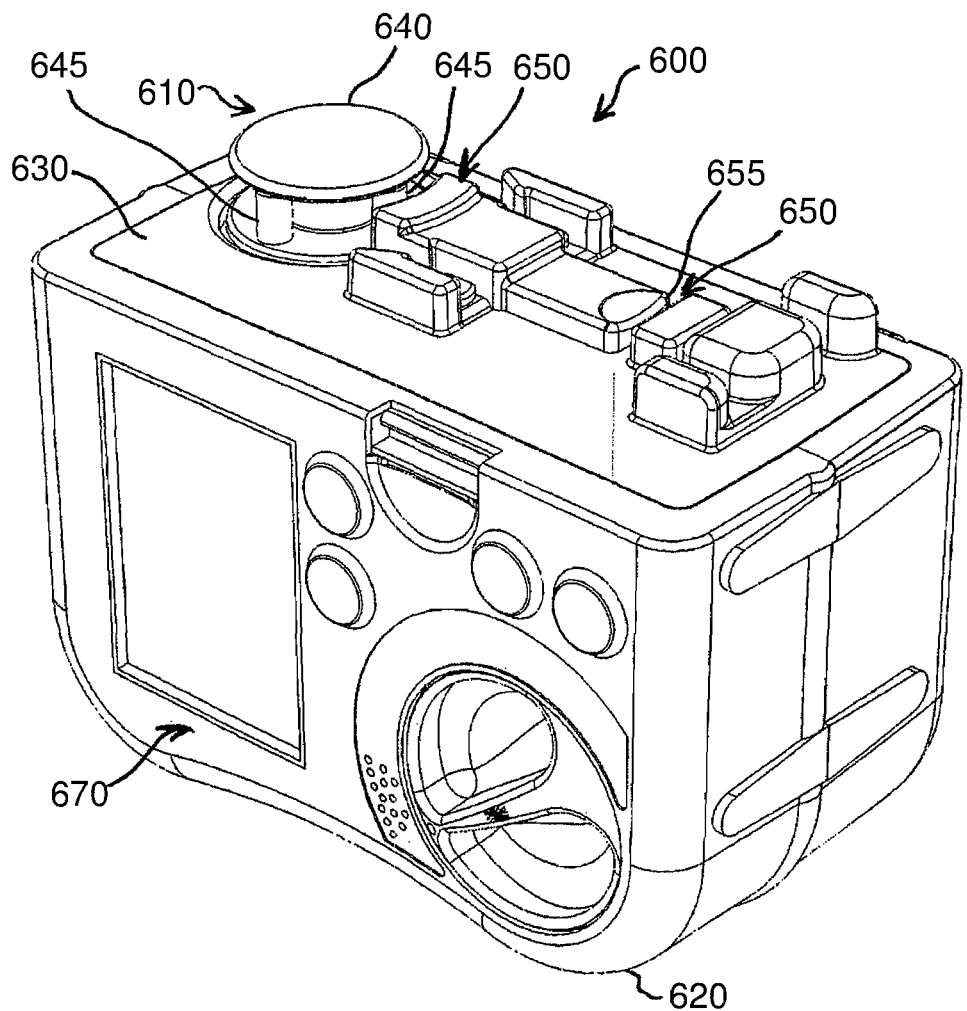
FIG. 15 illustrates the pump shown in FIGS. 13 and 14, with the cassette body removed for further illustration.

Turning now to FIGS. 13 through 26, and specifically now to FIGS. 13, 14, and 15, an optionally preferred configuration of an fluid delivery system 600 is shown. The delivery system may be used medically for enteral or parenteral applications, or for other applications outside of the medical context, such as the dispensing of fluids in a laboratory or other contexts where volume control is desirable.

Preferably, the enteral delivery system may include a peristaltic pump system 610 (FIGS. 14, 15) carried from a base 620. A mounting plate 630 is mounted to the base 620 and typically carries a rotor 640 having at least one or a plurality of peristalsis inducing rollers 645.

The mounting plate 630 may also include a mounting structure 650 that incorporates one or more capture walls or retainers 655 (FIGS. 15, 16) that enable the mounting structure 650 of the mounting plate 630 to receive and releasably hold a cassette of a feeding set, of which cassette body 703 is shown in FIG. 14. While not shown in FIGS. 13-14, the cassette may also include a pump tubing segment which extends from the cassette body and wraps around the rotor 640. Rotation of the rotor 640 pinches off portions of the pump tubing segment containing a solution and pushes the solution along the pump tubing segment, thereby pumping a fluid for delivery to a desired location, such as, for example, a beaker or a patient.

The enteral delivery system 600 also typically may include a mounting plate door 660 and releasable latch 665, which is shown in FIG. 13 in a closed position, but which has been removed for illustration purposes in FIG. 14 and FIG. 15.

In variations of any of the embodiments of a fluid delivery system 600, a pump controller subsystem 670 may also be included that can be remotely operated using Wi-Fi, Bluetooth®, and other types of wireless computer communications capabilities. The fluid delivery system 600 may also include a user display interface 680 that may incorporate a touch-sensitive screen to enable user interaction and control of the subsystem 670. The pump controller subsystem may also include actuators, rotary switches, buttons, and switches 690 as depicted in FIGS. 13 through 15 as well as in other of the various drawings and illustrations.

The fluid delivery system 600 may include a pump which is compatible with or specifically designed to receive part or all of a fluid delivery set, such as an infusion set or feeding set (collectively referred to as a feeding set). As shown in FIG. 13, the mounting plate 630 is typically configured to receive the cassette body 703 and pump tubing segment of a feeding set cassette. Such feeding sets 698 (FIG. 10) will typically include, among other components and features, the cassette 700, including a cassette body 703 which forms one or more connector portions 705, the pump tubing segment 710 (FIG. 10) and an inflow tubing 725 and an outflow tubing 730 which are connected by the connector portion to the pump tubing segment 710.

Figure 16:
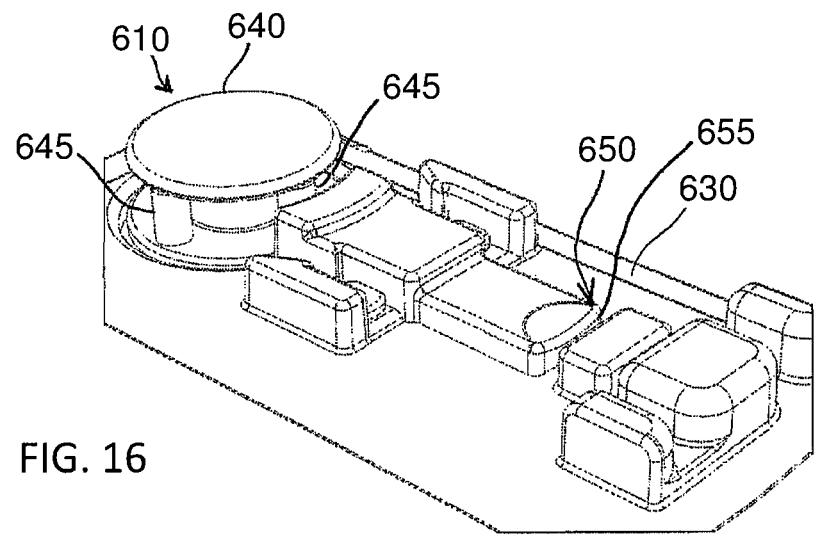
FIG. 16 is an enlarged detail view of the mounting plate as shown in FIG. 15.
Figure 17:
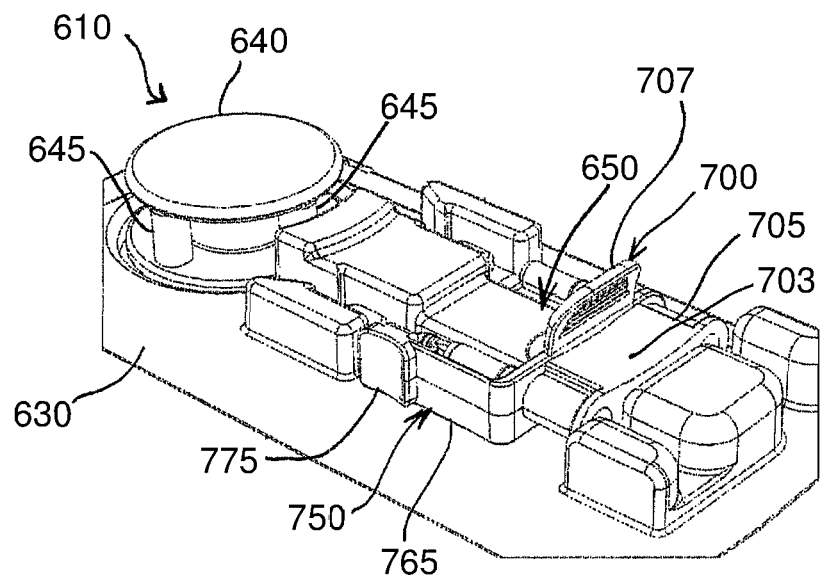
FIG. 17 is an enlarged detail view of the mounting plate and cassette body as shown in FIG. 14.
Figure 18:
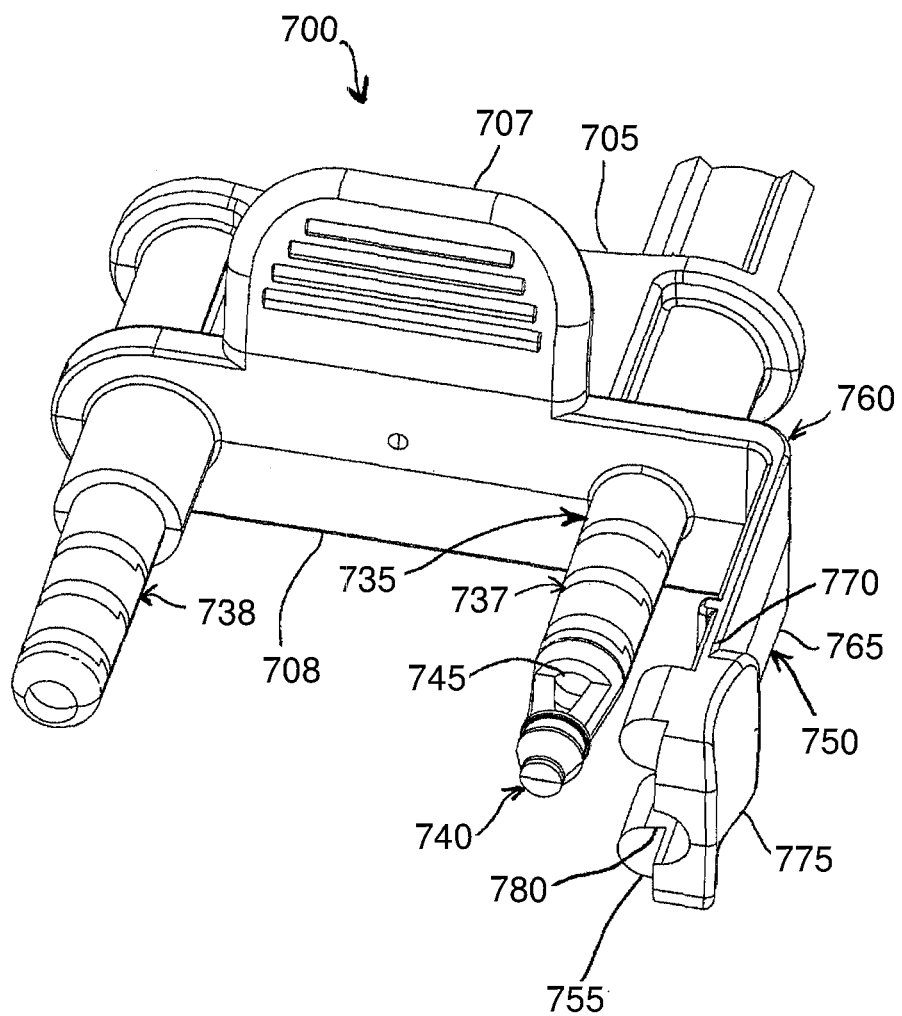
FIG. 18 is an enlarged, isometric, and rotated detail view of an embodiment of the cassette body of FIGS. 14 and 17.
Figure 19:
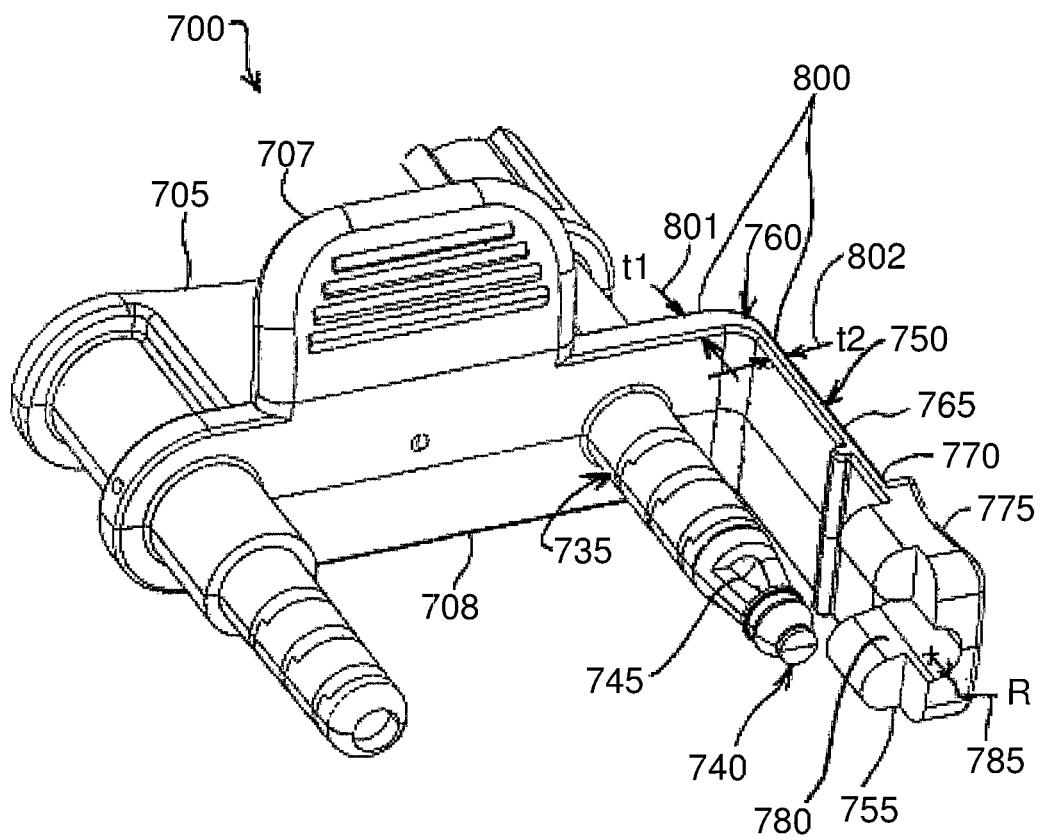
FIG. 19 is another rotated, isometric detail view of the cassette body of FIG. 18.
Figure 20:
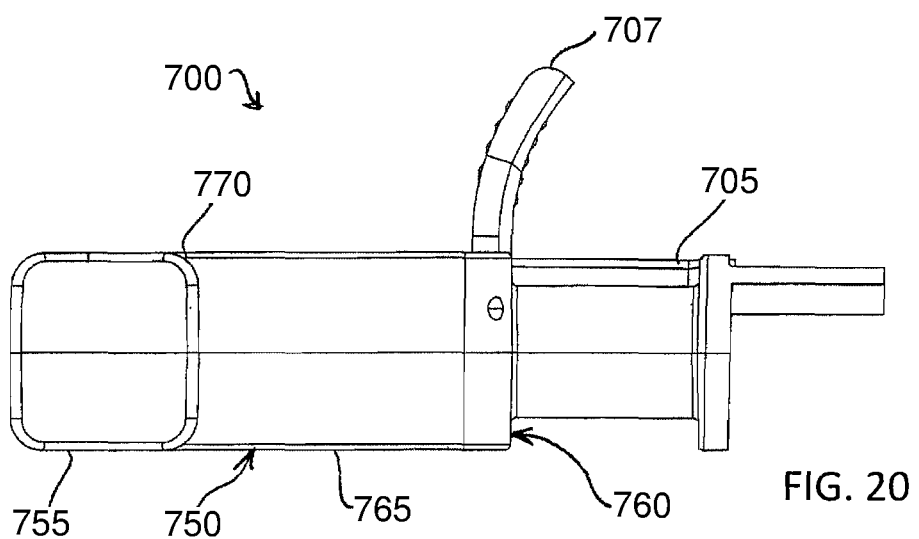
FIGS. 20 and 21 are rotated and opposite side details views of the cassette body of FIG. 14 and FIGS. 17 through 19.
Figure 21:
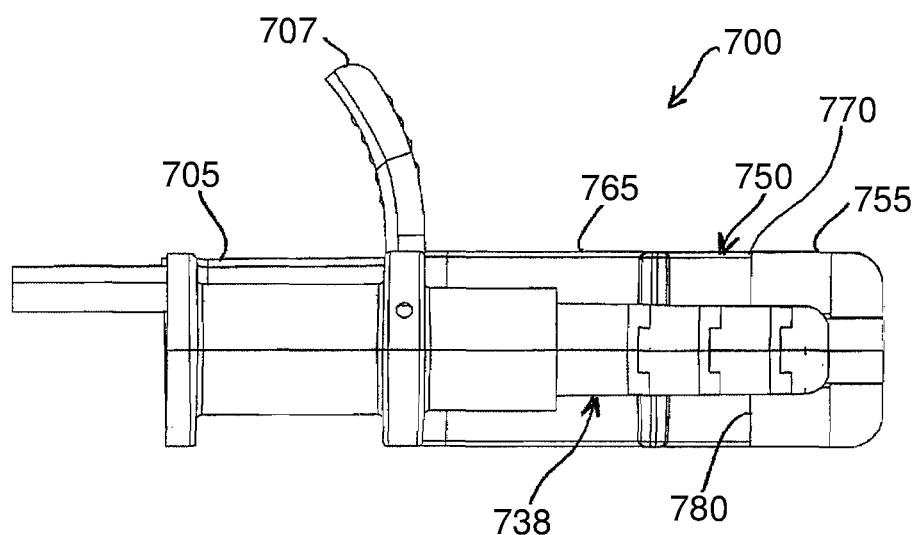

A grip 707 may also be incorporated as part of the cassette body 703 to enable manipulation of the cassette 700 of the feeding set 698. The cassette body 703 may also be adapted to have a retention lip 708 (FIG. 18) sized to be received and releasably captured in the mounting structure 650 of the mounting plate 630. The retention lip 708 can be positively biased against the capture wall 655 (FIGS. 15 and 16). With this modified arrangement, the cassette 700 of the enteral feeding set 698 may be removably and releasably received in and captured by the mounting structure 650 for cooperative use and operation with the pump system 610.

The cassette body 703 is preferably formed from a durable polymeric material that may be selected from the group that includes, for purposes of example but not for purposes of limitation, polypropylenes, polystyrenes, nylons, high-density polyethylenes, polycarbonates, acrylics, and similar polymeric materials. More preferably, the carrier or cassette body 703 is formed from such polymeric materials to have a hardness rating on the Shore durometer scales that is approximately about or approximately greater than about 85-95 on the Shore A-scale and/or about 40 to about 50 on the Shore D-scale.

With continued reference to the preceding illustrations, and with reference now also specifically to FIGS. 16 through 29, those having relevant knowledge in the technical field described here may comprehend that the carrier or cassette body 703 attaches to and carries a substantially flexible pump tubing segment 710 (see, e.g., FIG. 22) which has wall defining a lumen 713. The pump tubing segment 710 may be formed from any number of substantially flexible polymeric materials, which can include for purposes of example without limitation, silicone and or other elastomers, a polytetrafluoroethylene (PTFE), a polyvinyl chloride (PVC), or similar materials and combinations thereof.

In addition, such polymeric materials, when used to fabricate the pump tubing segment 710, will preferably and typically be selected to have a substantially flexible Shore durometer rating of approximately about 10 to about 50 Shore D-scale, and or about 10 to about 85 Shore A-scale.

More preferably, for purposes of operation and in cooperation with peristaltic pump system 610, the material of the pump tubing segment 710 may have a durometer rating suitable for the present application, including a range of at least about 30, including from about 45 to about 85, and also including from about 45 to about 65, and also including from about 60 to about 80, on the Shore A-scale. Of course, the flexibility of the pump tubing segment 710 will depend upon the specific material selected, the viscosity of enteral products to be pumped through the tubing, the geometric and physical configuration of and relationship between the pump tubing segment 710 and the rollers 645 of the rotor 640, and many other considerations and variables.

The pump tubing segment 710 includes a generally medial portion 715 positioned between the two ends attached to the cassette body 703 so that the pump tubing segment forms a substantially extensible peristalsis loop 720. The connector portion 705 of the cassette body 703 also connects the pump tubing segment 710 to the inflow line 725 and outflow line 730.

Although the pump tubing segment 710 is removed for illustration purposes from many of the figures described herein, the extensible or stretchable loop 720 is typically stretched about the rollers 645 of the rotor 640 and positively biased when the carrier or cassette body 703 is captured on the mounting plate 630 by the capture wall 655 of the mounting structure 650.

With continued reference to the various figures and illustrations and now also with specific reference to FIGS. 18 through 27, one of knowledge in the relevant fields of art may further comprehend that the feeding set 698 includes an inline valve 735 that is formed by the interaction of an occluder 740 and the walls of the pump tubing segment 710. Preferably, the material of the occluder 740 is selected from the group of materials described elsewhere herein and to have a hardness rating that is approximately and or substantially more rigid than, harder than, and/or higher than that of the material used to fabricate the pump tubing segment 710.

Selecting materials for the pump tubing segment 710 that are more flexible, more stretchable, or more ductile than the material selected for the inline occluder creates a relative material hardness, rigidity, or deformability differential between the tubing 710 and the occluder 740. In this way, the walls of the tubing segment 710 may be easily stretched, flexed, or deformed without a corresponding and or comparable deflection, deformation, and/or flexure of the inline occluder 740. Deformation of the tubing 710 allows a channel to open between the inner wall of the tubing and the stop or occluder 740. By selectively controlling the interaction of the tubing 710 and the occluder, a valve 735 is formed.

Figure 22:
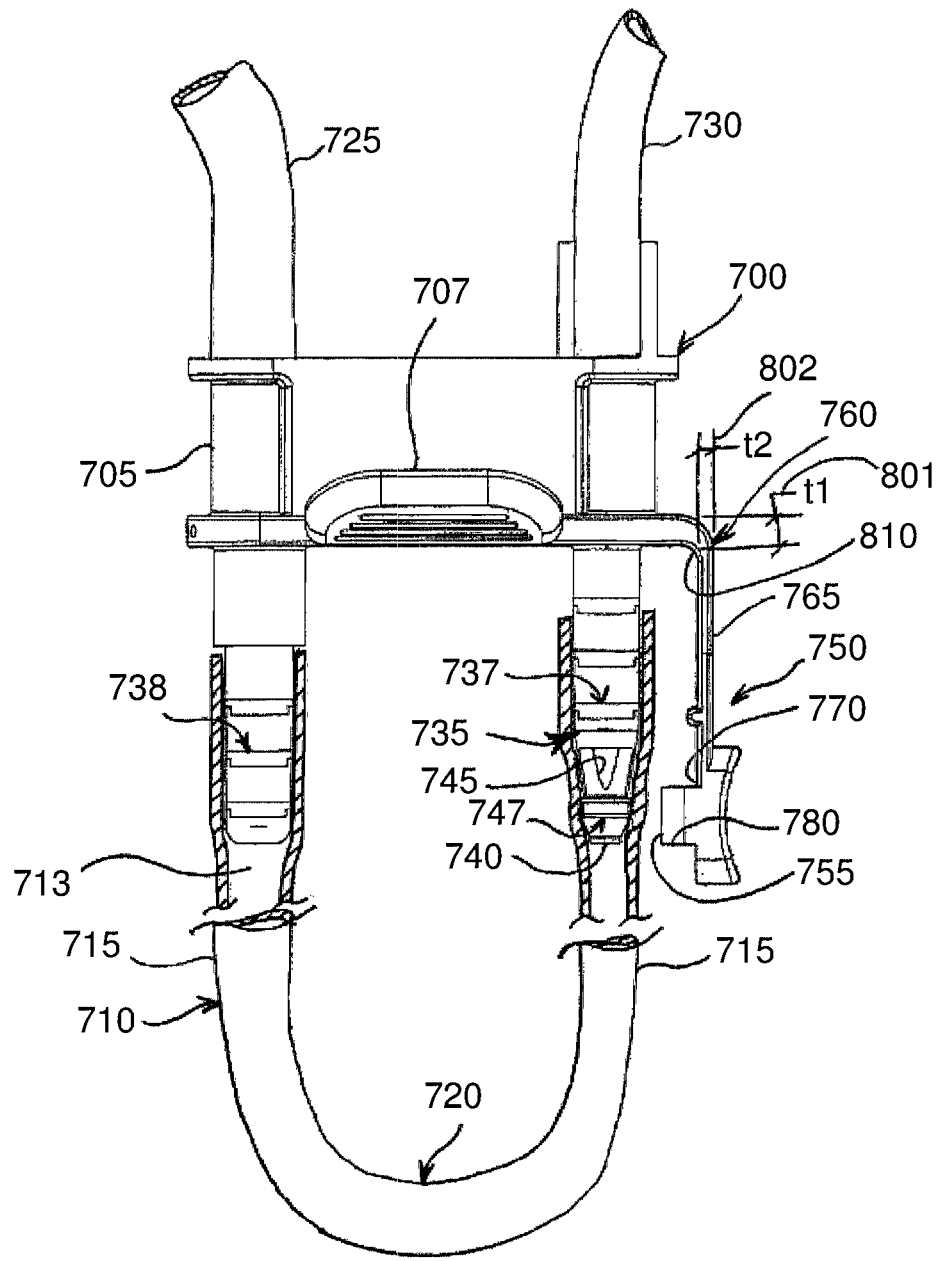
FIG. 22 is a top view of a feeding set cassette including the cassette body and shown in FIG. 14 and FIGS. 17 through 21 and a pump tubing segment.
Figure 23:
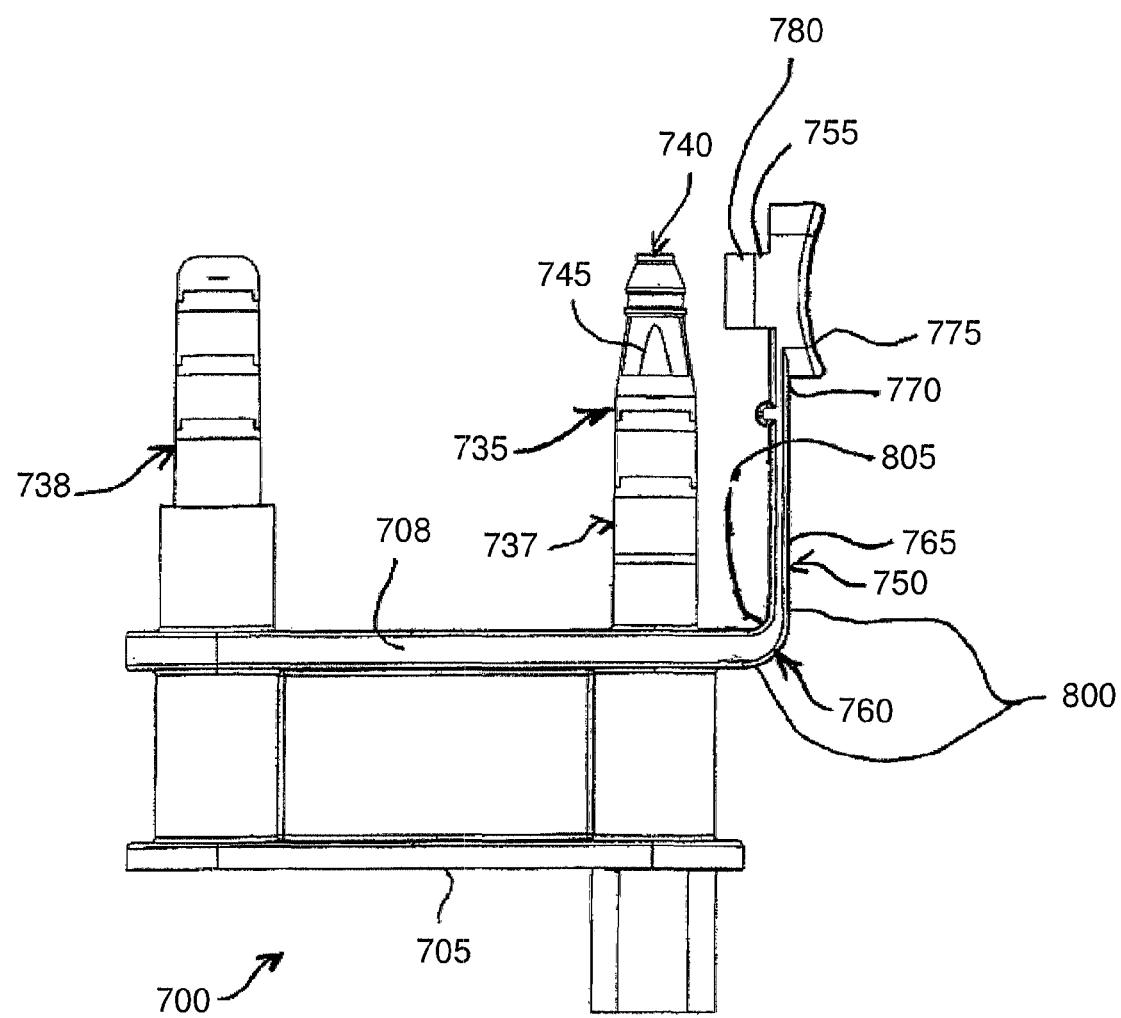
FIG. 23 is rotated lower and enlarged view of the cassette body illustrated in FIG. 14 and FIGS. 17 through 22.

The various figures depict the interaction of the tubing 710 and the occluder 740 which form the valve 735. The connector portion 705 of the cassette body includes a connector 737 with a bore or lumen therethrough which opens in a port 745 adjacent the stop or occluder 740. The pump tubing segment 710 adjacent the occluder 740 prevents flow past the stop and into the port 745 unless the tubing is expanded away from the stop sufficiently to form a flow channel. This may be accomplished by an increase in pressure in the tubing sufficient to expand the tubing radially, or by pressing on the tubing to open a flow path around the stop or occluder 740. As shown in FIG. 22, the occluder 740 may include one or more annular ribs 747 to facilitate sealing with the interior of the tubing. It will be appreciated that the occluder 740 can be placed in other positions along the pump tubing segment 710 or even extending into the inflow line 725 or the outflow line 730.

The enteral feeding set 698 also preferably includes a deflectable primer or actuator 750. The actuator 750 may be formed and/or included about the mounting plate 630 of the pump system 610, and may also preferably be formed on or about the cassette body 703. In the variations where incorporated on or about the cassette body 703, the primer or actuator 750 may include at least one actuation pad or engagement member 755 and may extend from a flex joint 760 of the cassette body 703. The flex joint 760 may further preferably include a flexible arm or deflection stanchion 765 that projects to an extent 770 adjacent the occluder.

At least one engagement member 755 may further incorporate a pair of projections 780 extend and form an arcuate recess defining a channel for receiving a portion of the tubing segment. The recess may be formed to define a radius, R, 785 (FIGS. 19 & 24) along at least a portion thereof that is about the same size and preferably slightly narrower than the outer diameter of the tubing segment, and more preferably narrower than the outer diameter of the occluder. As the projections of the engagement member engage the tubing segment, they deform or distend the tubing and thereby open a flow channel on the opposing side of the tubing segment, thereby allowing fluid flow.

The flex joint 760 may be fabricated using a number of different configurations. In one arrangement, the flex joint 760 is made with at least one load distributor 800 adapted to withstand and distribute the dynamic stress and loading experienced during flexure of the actuator arm 765. In this exemplary variation, the at least one load distributor 800 is formed to have varying thicknesses t1, 801, and t2, 802 (FIGS. 7 and 10) wherein t1, 801 is approximately thicker than t2, 802.

In this configuration, a constant force applied to the actuator arm 765, enables the portion having thickness t1, 801, to bend less than the portion having thickness t2, 802. As the thickness varies and increases between these portions from t2, 802, to t1, 801, the additional material available in a cross-sectional area better distributes the load force and material stress and strain into the structure of the cassette body 703.

Additionally, the configuration of the thicknesses and geometry of the one or more load distributors 800 or flexure reinforcements may enable or impart a threshold load requirement upon and to the deflectable primer or priming actuator 750. In this way, the priming actuator or deflectable primer 750 will not deflect and enable priming of the lumen 713 without imposition of possibly desirable, threshold or pre-established or predetermined load conditions. This capability can prevent undesired and or inadvertent actuation, as well as inadvertent priming of the lumen 713. All of these modifications to the configuration of the flex joint 760 may be further benefited by minimization of stress and strain concentrations around the joint 760 by use of wide, generous, or large radii 810 that connect the contemplated load distributors or reinforcement 800 to the cassette body 703.

The at least one actuation pad or engagement member 755 of the priming actuator 750 is also preferably positioned about the cassette 700 to be cooperatively positioned proximate the inline valve 735 formed by the occluder 740 and the pump tubing segment 710. With continued reference to the aforementioned figures, reference is also now specifically made to FIGS. 28 and 29.

Figure 28:
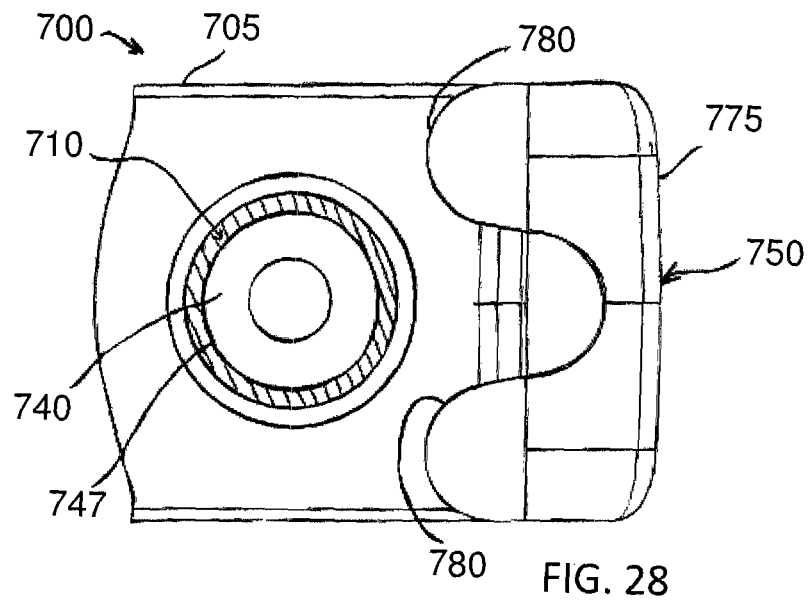
FIG. 28 is an enlarged rotated detail end view of the portion of the cassette depicted in FIGS. 26 and 27.
Figure 29:
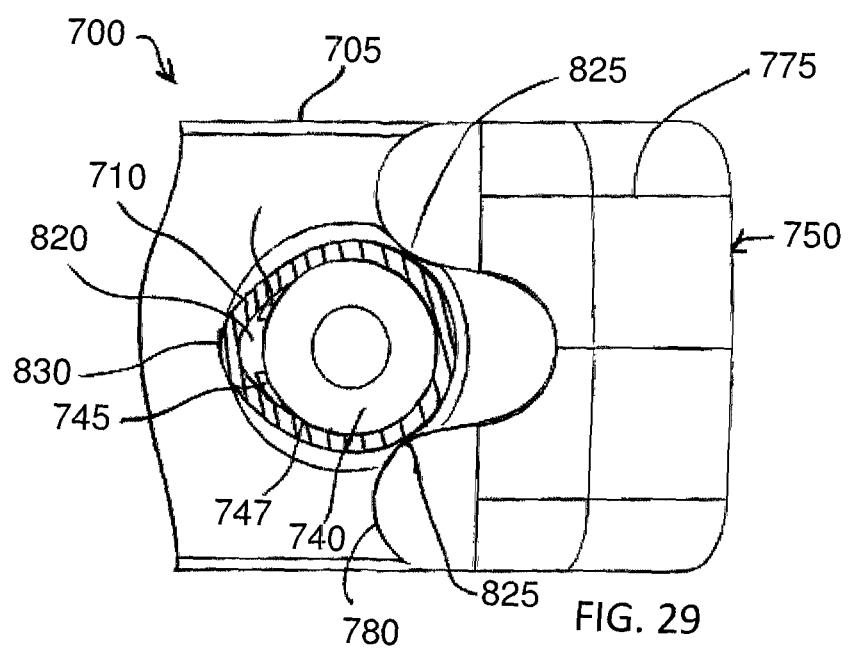
FIG. 29 is another view of the portion of the cassette of FIG. 28, but with the actuator deflected against the pump tubing segment so as to distend the tubing and open a flow path past the occluder.

In these figures, those with an understanding of the technical field of art may further appreciate that the primer or actuator 750 can be actuated from a nominal at rest position shown in FIG. 28, to a deflected or actuated position that is schematically illustrated in FIG. 29. In the deflected or actuated position of FIG. 29, the projections 780 and channel formed thereby of the at least one engagement member 755 is urged into contact with the pump tubing segment 710.

The portion of the pump tubing segment 710 adjacent the occluder 740 is thereby sandwiched between the projections of the engagement member and occluder and deforms to establish at least one flow channel 820. Establishment or formation of the at least one flow channel 820 enables fluid communication between the opposite inflow and outflow lines 725, 730 and through the lumen of the pump tubing segment 710 and the valve port 745.

In one exemplary configuration of the at least one flow channel 820, the walls of the tubing 710 defining the lumen are stretched against the exterior of the occluder 740 or annular ribs 747 by the channel and projections 780 of the engagement member 755, which forms at least one deformed or flexed or deflected or stretched portion 825 of the tubing wall. As a result, at least one complementary relaxed, bunched, or distended portion 830 of the wall of the pump tubing segment 710 also forms proximate thereto (FIG. 29).

The inline valve 735 formed by the tubing segment 710 and occluder 740 is shown for exemplary purposes in the various illustrations to be along the cassette 700 adjacent the connection with the outflow line 730. The primer or actuator 750 is also shown to be cooperatively proximate to the valve 735. However, the valve 735 and the primer 750 may also be disposed adjacent the connection to the inflow line 725.

The actuator 750 may or may not be included about or on the cassette body 703 of the cassette 700, and may also and/or instead be incorporated about the mounting plate 630. In this alternative adaptation, the actuator 750 may actuate the inline valve 735 upon insertion of the enteral feeding set 698 on the mounting plate 630.

Figure 30:
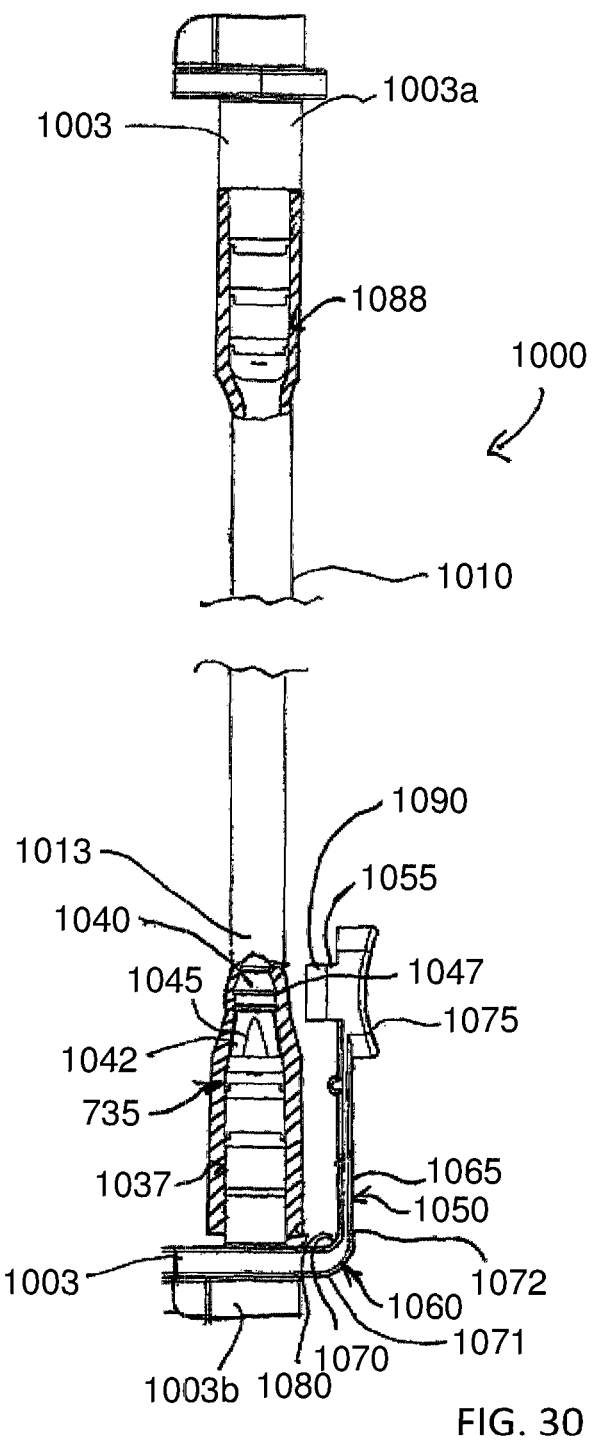
FIG. 30 shows a partial cut-away top view of a fluid delivery cassette for an linear or curvilinear peristaltic pump in accordance with the principles of the present invention.

While the principles of the present invention have been discussed above generally relating to rotary peristaltic pumps, it will be appreciated that the various aspects of the present invention can also be used with other peristaltic delivery systems including linear and curvilinear peristaltic pumps. Turning to FIG. 30, there is shown a top, partially cut-away view of a cassette 1000 for use in linear or curvilinear peristaltic pumps. The cassette 1000 includes a pair of cassette bodies 1003 which are attached to opposing ends of a pump tubing segment 1010.

Each of the cassette bodies 1003 includes a connector. Cassette body 1003a includes a standard connector 1038, while cassette body 1003b includes a connector 1037 which has an occluder 1040 which may be attached thereto by a pair of arms 1042 or other attachment structure, similar to the configuration shown in FIG. 30, so that the connector has a bore leading to a fluid flow port 1045 adjacent the occluder. The occluder 1040 may include annular ribs or barbs 1047 or be otherwise formed to engage a portion of the tubing segment 1010 and form a seal which prevents flow through the lumen 1013 of the tubing under ambient conditions. Thus, the portion of the tubing segment 1010 and the occluder 1040 form an inline valve which prevents flow through the lumen of the tubing segment unless the tubing segment is distended to open a flow channel around the occluder.

Also shown in FIG. 30 is a deflectable priming actuator 1050 which is formed by a projection which may be formed integrally with the cassette body 1003b. The actuator 1050 may include at least one actuation pad 1055 and may extend from a flex joint 1060 of the cassette body 1003b. The flex joint 1060 may further include a flexible arm or deflection stanchion 1065 that projects along the tubing segment 1010.

The actuator 1050 may include a recess 1075 for engagement by a user and at least one actuation pad or engagement member 1055 may further incorporate one or more projections 1090 which form a channel with a changing width. While not shown in FIG. 30, the engagement member may include a pair of rounded projections which help to maximize engagement with the tubing segment to cause deformation/distension adjacent the occluder 1040 as discussed below. A position along the projections forms a recess (as shown in FIGS. 28 and 29 which has a radius along the recess which is similar to the radius of the occluder 1040. The rounded nature of the projections, the sloping sidewalls and wall structure forming the recess help to distend the tubing segment (as shown in FIG. 29) and open a flow channel between the inner wall of the tubing segment (710 in FIG. 29) and the occluder (740 in FIG. 29).

The flex joint 1060 may be fabricated using a number of different configurations. In one arrangement, the flex joint 1060 is made with at least one load distributor 1070 adapted to withstand and distribute the dynamic stress and loading experienced during flexure of the arm 1065. In this exemplary variation, the at least one load distributor 1070 is formed to have varying thicknesses t1, 1071, and t2, 1072, wherein t1 is approximately thicker than t2. Other flex joints are known and their application will be apparent in light of the present disclosure.

This configuration, for a constant force applied to the flexible arm 1065, enables the portion having the greater thickness to bend less than the portion which is thinner. As the thickness varies and increases between t1 1071 and t2 1072, the additional material available in cross-sectional area better distributes the load force and material stress and strain into the structure of the cassette body 703b.

In other variations, the at least one load distributor 1080 may also be formed as or with, incorporate, or be augmented by, at least one flexure reinforcement 1085. This other type of load distributor 1070 and or flexure reinforcement 1085 may be formed with a thickness, a length, and a width that enables a further stress/strain load path between the flexure arm or deflection stanchion 1065 and other portions of the structure of the cassette body 1003b.

Additionally, the configuration of the thicknesses and geometry of the one or more load distributors and/or flexure reinforcements 1070 may enable or impart a threshold load requirement upon and to the deflectable primer or priming actuator 1050. In this way, the priming actuator 1050 will not deflect and enable priming of the lumen 1013 without imposition of a desired threshold force in order to prevent undesired and or inadvertent actuation, as well as inadvertent priming of the cassette 1000.

While not shown in FIG. 30, the connectors 1037 and 1038 or other portion of the cassette bodies 1003 may be connected to an inflow line (i.e. upstream) and a outflow line (downstream) to form a feeding set.

Figure 31:
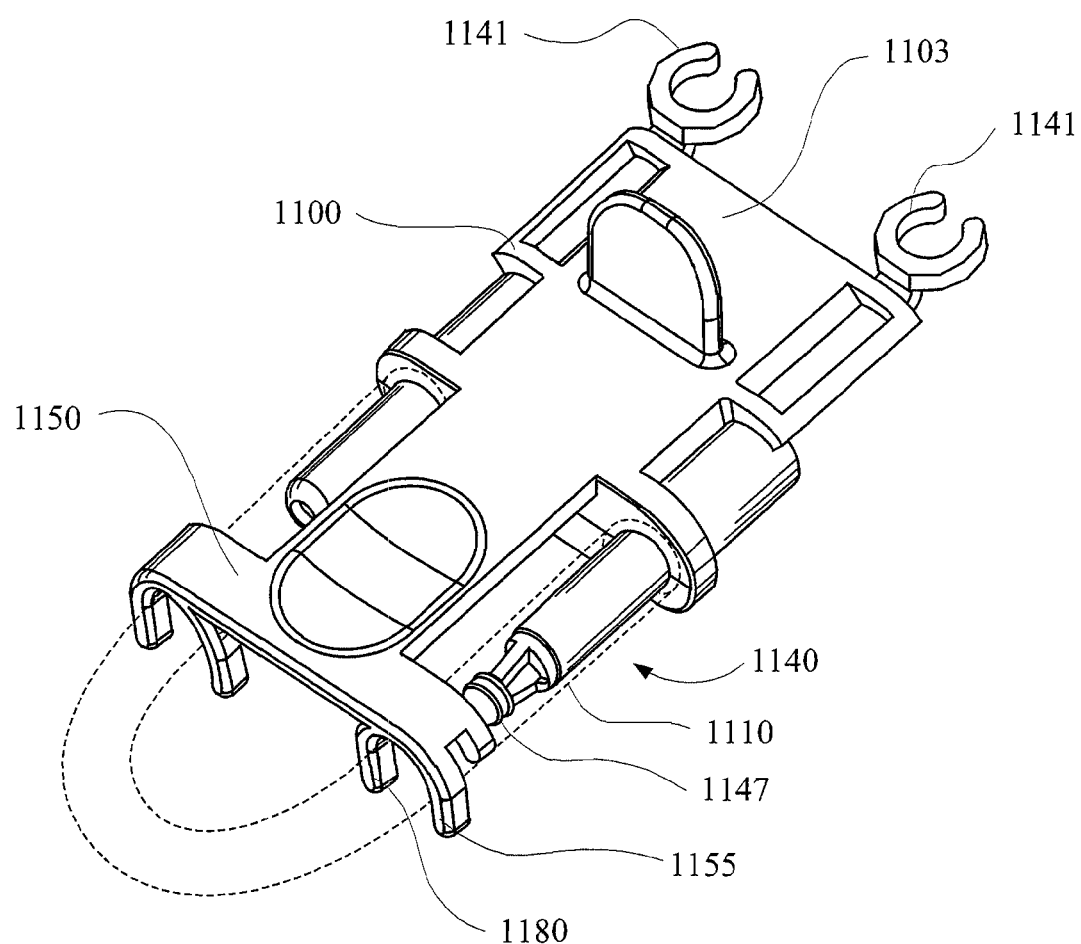
FIGS. 31 and 32 show a perspective and side views of an alternate embodiment of a cassette formed in accordance with principles of the present invention.

Turning now to FIG. 31, there is shown an alternate embodiment of a cassette 1100 which may be used with peristaltic pumps. The cassette includes a cassette body 1103 with an occluder 1140 extending therefrom. The occluder has a stop 1147 which is disposed in a tubing segment, shown by dashed lines 1110. An actuator 1150 forms an arm which extends from the cassette body 1103 generally parallel to the tubing segment and engages the tubing segment a short distance beyond the stop. When the arm of the actuator 1150 is pressed downwardly, an engagement member 1155 on the arm presses downwardly on the tubing segment 1110 and deforms the tubing segment to thereby open a flow channel with the lumen of the tubing segment past the stop 1147 of the occluder. The engagement member 1155 may include projections 1180 for holding the tubing segment. Thus a person using the pump is able to prime the cassette 1100 with fluid by simply pressing downwardly on the actuator 1150 so that the engagement member 1180 contacts and deforms the tubing. The configuration of the actuator 1150 allows both sides of the cassette to be primed in the event that it was desired to have an occluder both upstream and downstream from the peristalsis loop.

The cassette body 1103 also shows a pair of retainers 1141. The retainers can be used to hold the inflow and outflow lines (not show) attached to the cassette.

Figure 32:
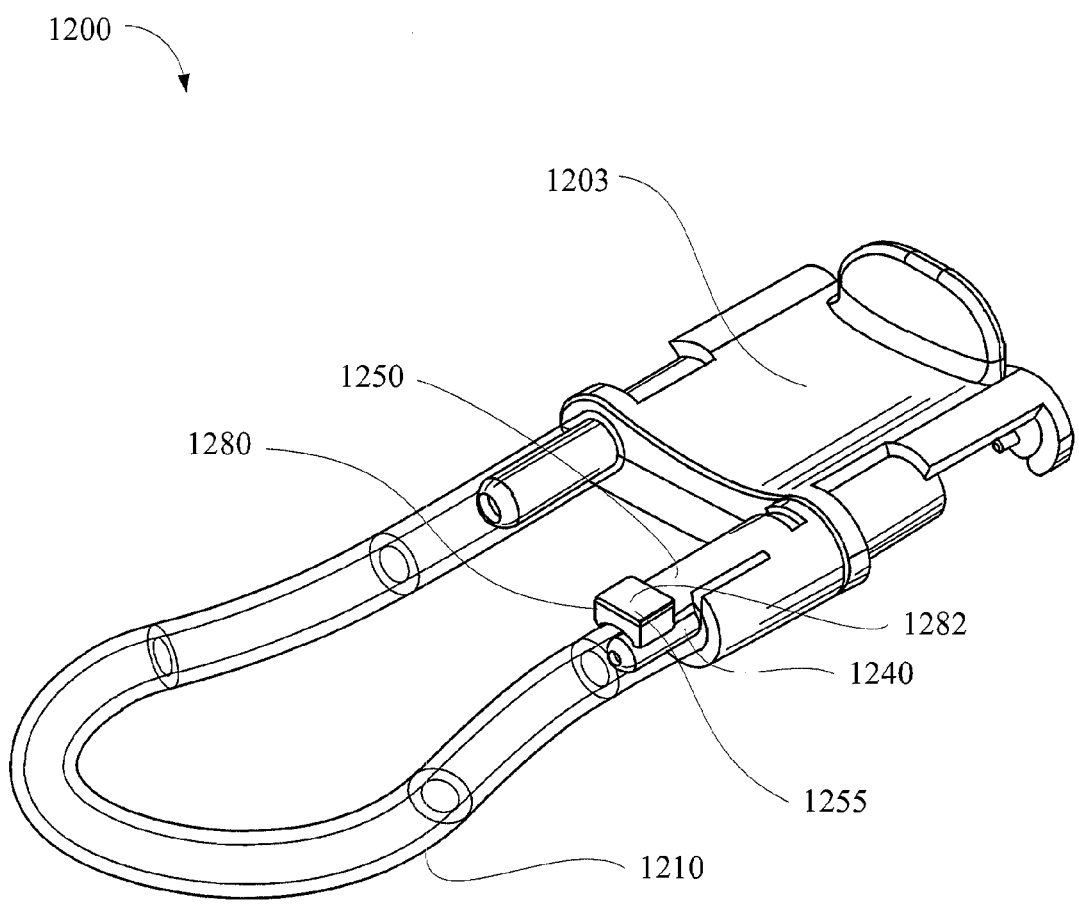
Figure 35:
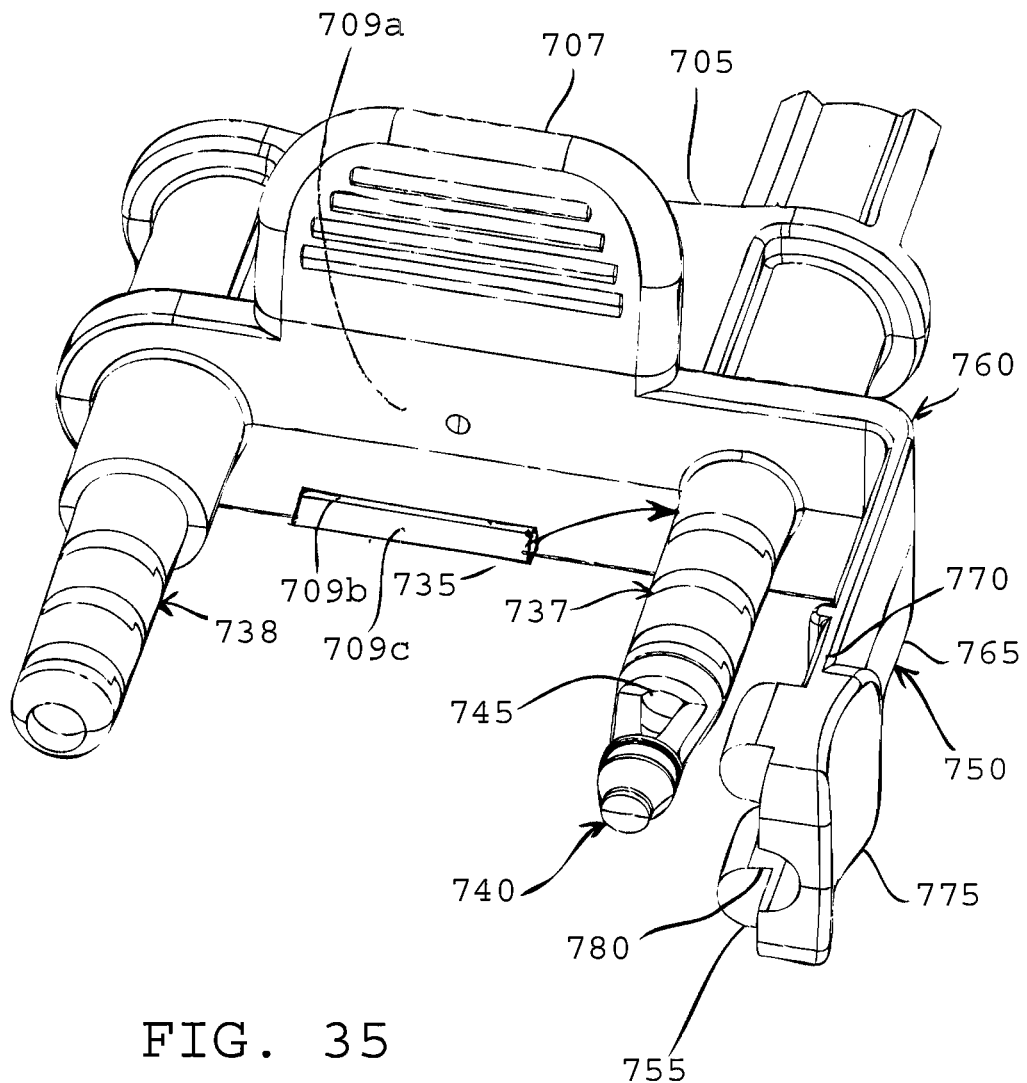
FIG. 35 shows an enlarged front side perspective view of a cassette body formed in accordance with the engagement surfaces shown in FIG. 26.

FIG. 32 shows an alternate embodiment of an actuator 1250. The actuator 1250 is not formed integrally with the cassette body 1203. Rather, it is formed as a separate piece and then attached so as to be disposed adjacent the occluder 1240. Disposed on the arm forming the actuator 1250 is an engagement member 1255 which may include projections 1280, for engaging and deforming the tubing to open a flow path. Opposite the engagement member 1255 is a shaped recess 1282. In use, a person presses their finger into the shaped recess to force the engagement member 1255 of the actuator 1250 into engagement with the tubing segment 1210 to thereby deform the tubing and open a flow channel between the tubing segment and the occluder 1240. Pressing on the recess 1282 moves the engagement member 1255 into contact with the tubing segment and deforms the tubing segment to open a flow channel between the tubing segment and the stop to thereby allow flow through the infusion set. In each of these embodiments, release of pressure on the actuator allows the actuator to move away from the tubing segment so that the tubing segment returns to its normal orientation and precludes flow.

One issue which is present in the mounting of a cassette body in a peristaltic feeding pump is ensuring that the cassette is properly positioned within the mounting structure With reference to FIGS. 33 through 36, there are shown alternate aspects of the engagement between the mounting structure 650 of the pumping mechanism 610 and the engagement surface on a projection of the cassette body 703. The mounting structure 650 includes the capture wall 655'. The capture wall 655' has a plurality of segments 655a, 655b and 655c as to form a multi-faceted engagement surface. The first or upper portion 655a of the capture wall 655' may be vertical or inclined. The second or lower portion 655c of the capture wall 655' is sloped at a desired angle typically less than 15 degrees from vertical (or the general alignment of the pump body) and typically between 3 and 10 degrees and most typically about 5 degrees. Between the upper portion 655a and the lower portion 655c of the capture wall 655' is a substantially horizontal third or middle portion 655b which is typically disposed between about horizontal and 15 degrees from horizontal, typically between 3 and 10 degrees and most typically about 5 degrees from horizontal. In other words, the third portion is generally perpendicular to the other two portions.

Likewise, the front of the connector or the cassette body 703 is provided with a multi-angled engagement surface 709'. The first, upper portion 709a may be vertical or substantially vertical and is preferably angled complementary to the upper portion 655a of the capture wall 655'. A second, lower portion 709c is sloped at an angle which is generally complementary to the lower portion 655c of the capture wall 655. The third, middle portion 709b is sloped slightly above horizontal, i.e. 0-15 degrees and typically between about 3 and 10, and most typically 5 degrees, i.e. generally perpendicular to the other two portions.

In an ideal situation, a person loading a peristaltic pump would push the cassette 703 all the way into the pump so that the engagement surface of the cassette engaged the engagement surface of the mounting structure 650 on the pump 610 and thereby ensured that the cassette 703 would not come out. However, it is not uncommon for medical personnel or a patient to fail to completely load the cassette 703 into the pump 610. The engagement surfaces 655a, 655b 655c, 709a, 709b and 709c interact with one another under tension to encourage the cassette body 703 to slide downwardly relative to the capture wall 655' until an engagement member defined by the lower portion 709c and middle portion 709b of the engagement surface snaps into place in the angled void defined by the lower portion 655c and middle portion 655b of the capture wall 655'.

Figure 36:
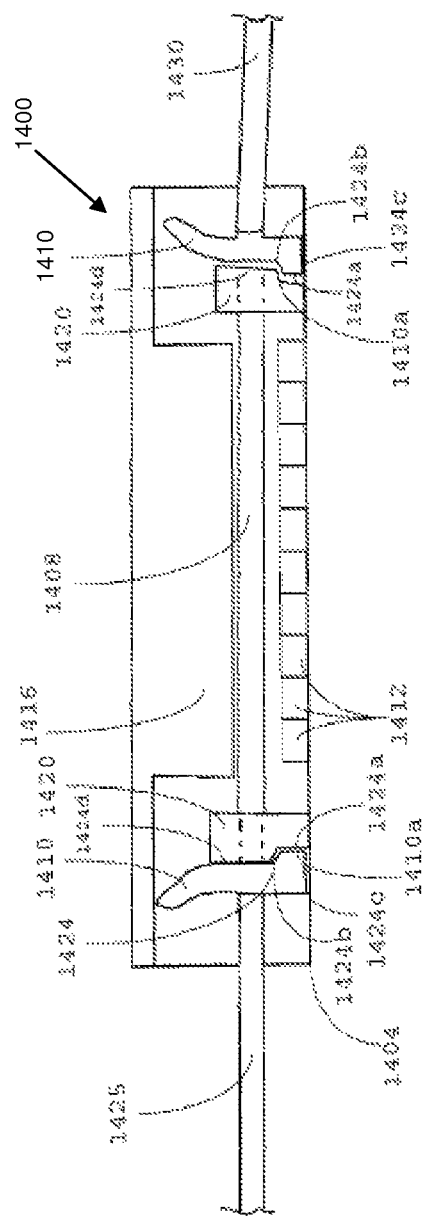
FIG. 36 shows a side, fragmentary view of a cassette formed for a linear or curvilinear peristaltic pump and a pump body for receiving the same.

With reference to FIG. 36, there is shown a fragmentary view of a cassette 1400 formed for a linear or curvilinear peristaltic pump and a pump body 1404. The cassette 1400 includes a pair of connectors 1410 which connect a pump tubing segment 1408 to an inflow line 1425 and an outflow line 1430. The pump tubing segment 1408 is engaged by a plurality of fingers or keys 1412 which compress the tubing against a platen 1416 to thereby force fluid out of the tubing segment and through the outflow line 1430.

One or both of the connectors 1410 of the cassette 1400 have an engagement member 1424 or projection which engages engagement surfaces on the mounting structure 1420 on the pump body 1404. The engagement member 1424 includes projection which has a first, lower engagement surface 1424a disposed at the lower portion end of the connector 1410. The lower engagement surface is angled between 0 and 15 degrees, and more typically between about 3 and 5 degrees. The projection also includes a second angled face which forms a middle engagement surface on the connector 1410. The middle engagement surface 1424b may be disposed between 0 and 45 degrees relative to horizontal, typically between about 3 and 15 degrees, and often about 5 degrees. The bottom of the projection 1424c is generally flat and engages the bottom of the mounting structure into which the connectors 1410 are placed.

The connectors 1410 may also include an upper portion 1424d of an engagement surface extending from the projection 1424. The engagement surface may be vertical, or may be sloped from vertical, typically between 3 and 10 degrees. The upper surface 1424d and the engagement surfaces 1424a and 1424b of the projection, are preferably complementary to an upper engagement surface 1420a, a middle engagement surface 1420b and a lower engagement surface 1420c, respectively, which are formed on the mounting structures 1420. The complementary engagement surfaces urge the connectors 1410 downwardly when placed under tension by the stretched pump tubing segment 1408. Thus, the connectors tend to slide down along the mounting structures 1420 and then snap in place when the void formed by the middle and lower engagement surfaces toward the bottom of the mounting structures aligns with the projection 1424 extending from the bottom portion of the connectors 1410.

Figure 37:
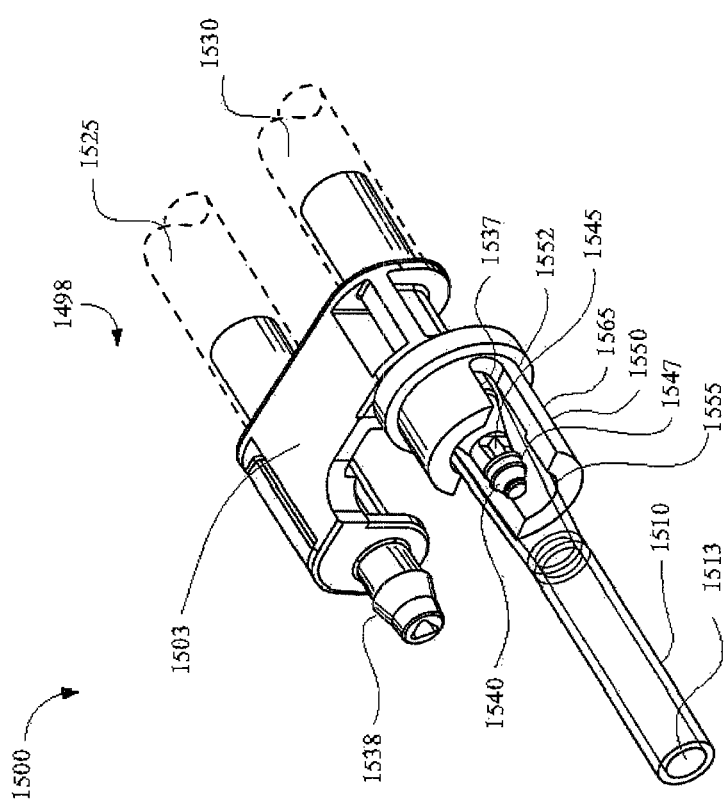
FIG. 37 shows a perspective view of another embodiment of the cassette of the present invention.

Turning now to FIG. 37, there is shown a perspective view of another embodiment of a cassette 1500 for use with a peristaltic pump as part of a feeding set, an infusion set, or for dispensing liquids in a non-medical environment. The cassette 1500 includes a pump tubing segment 1510 which is attached to a cassette body 1503. The cassette body includes a connector 1538 which attaches to one end of the pump tubing segment 1510 and another connector 1537 which attaches to the opposing end to form a loop. The two connectors 1537 and 1538 are attached together and formed integrally with the cassette body. In use, the loop formed by the tubing segment 1510 can be placed around a pump rotor and then pulled until the cassette body 1503 can nest in a mounting structure similar to the cassette body shown in FIG. 14.

The second connector 1537, which is typically disposed downstream from the pumping mechanism, but which may be disposed operationally on either side of the pumping mechanism, includes an occluder 1540. When the tubing segment 1510 is disposed on the connector 1537, the occluder 1540, and in particular a stop of the occluder, is disposed within the lumen 1513 of the tubing segment. The stop is larger than the interior diameter of the tubing segment 1510 so as to block flow through the lumen 1513 of the tubing segment unless the tubing segment is deformed by pressure within the tubing or an outside pressure is placed on the tubing segment to deform it and thereby form a flow channel between the stop and the wall of the tubing segment.

The description regarding the prior embodiments relating to the materials and interactions of the tubing segment, occluder and an actuator of the other embodiments are equally applicable in the present embodiment and are incorporated herein by reference.

The embodiment shown in FIG. 37 includes an actuator 1550 which is attached to the cassette body 1503. The attachment can be performed by known means including, but not limited to, press-fit, snap-fit, adhesives, melting or other types of bonding. The actuator 1550 includes an arm 1565 which extends along the tubing segment 1510 from the main portion of the cassette body 1503 to a location adjacent the occluder 1540. The arm 1565 may extend parallel the tubing segment or may have some other shape.

Disposed along the arm 1565 is an engagement member 1555 which is configured to engage the tubing segment 1510 to deform or distend the tubing segment and thereby open the flow channel.

Figure 38:
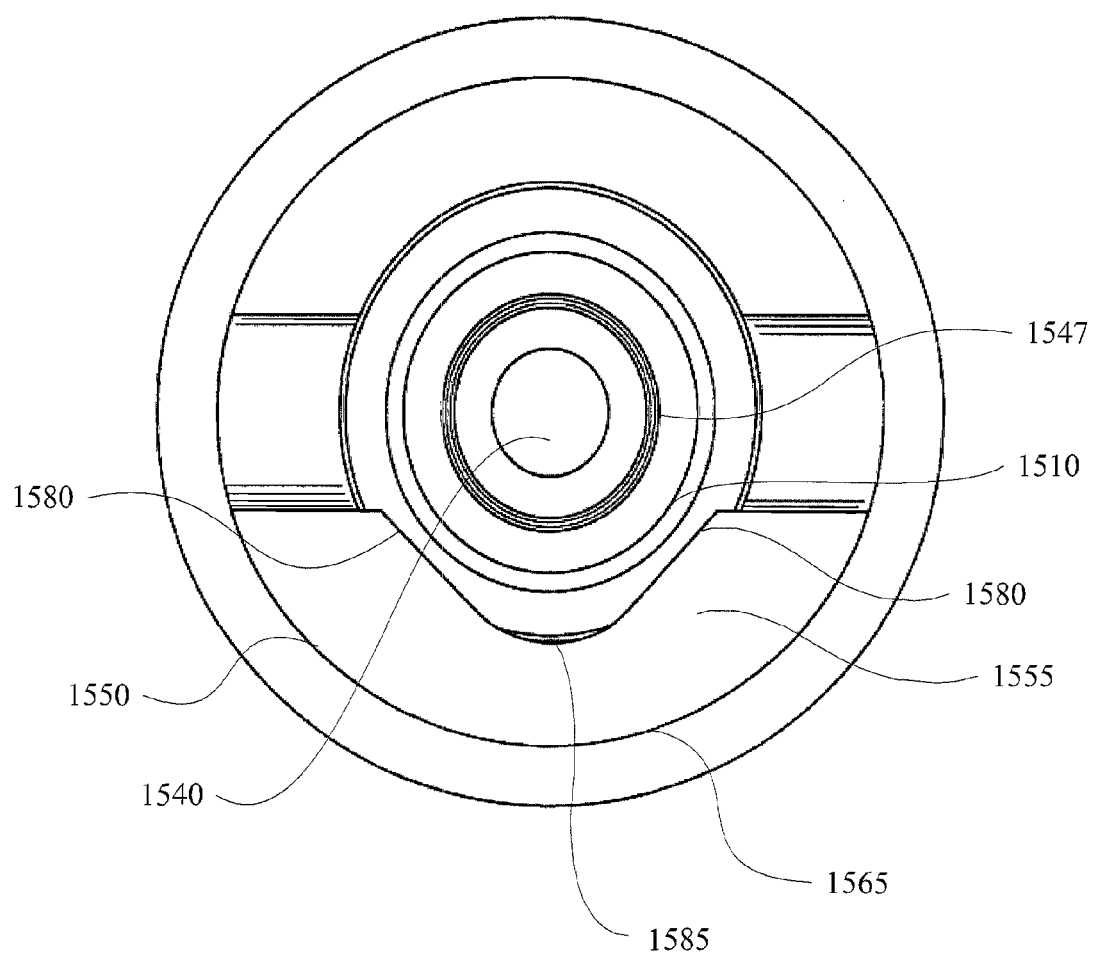
FIG. 38 shows an end view of the actuator and occluder shown in FIG. 37.
Figure 39:
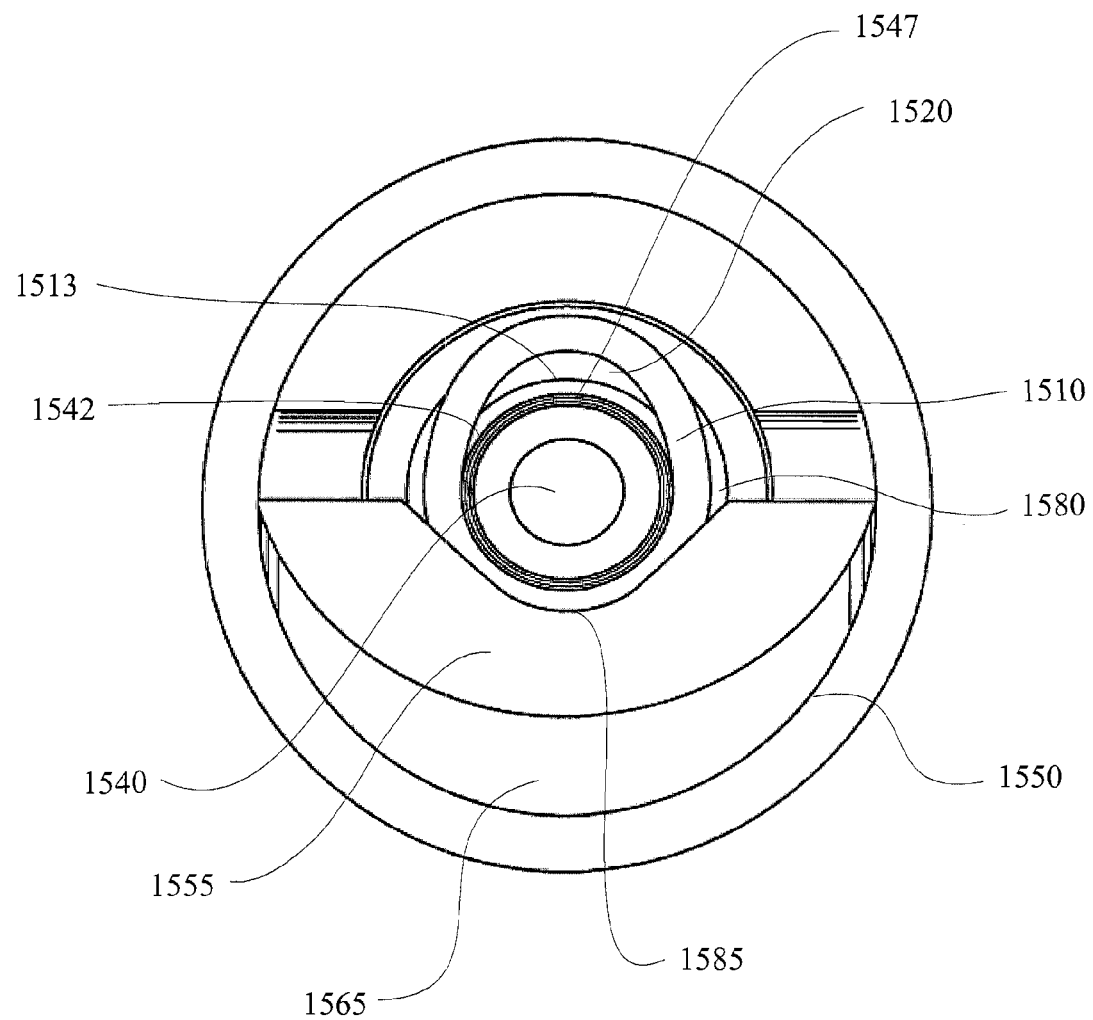
FIG. 39 shows an end view similar to that of FIG., but with the actuator deflected to engage the tubing segment and open a flow channel past the occluder.

As shown in FIGS. 38 and 39, the engagement member 1555 includes projections 1580 or projecting side members which define a channel 1585 for receiving at least a portion of the tubing segment 1510 and the occluder 1540.

The actuator 1550 works by forcefully engaging the tubing segment 1550 with the engagement member 1555 adjacent the occluder 1540 and deforming the tubing segment so that a flow channel 1520 forms between the occluder 1540 and the tubing segment 1510 opposite the actuator as discussed above and shown with respect to FIG. 29. Ideally, though not required, a single flow channel is formed past the occluder 1540, thereby allowing flow through the lumen 1513.

The interaction between the tubing segment 1510 and the occluder 1540 forms a valve 1535 which is biased closed until opened by the application of force on the actuator 1550. As soon as the force is released, the resilient tubing segment 1510 will return to its normal shape and engage the occluder 1540 to stop flow through the lumen.

It will be appreciated that the arm 1565 of the actuator 1550 may be made from a flexible material such as plastic. The flexible material is able to flex at a joint 1552 so as to deflect from a first position, wherein it is positioned away from the tubing segment 1510, into a second position wherein it forcefully engages the tubing 1510 and opens the flow channel past the occluder 1540.

The tubing segment 1510 adjacent the occluder 1540 is presented in shadow in order to show the connector 1537 in additional detail. The connector 1537 has a bore or lumen therethrough which opens in a port 1545 adjacent the stop or occluder 1540. The pump tubing segment 1510 adjacent the occluder 1540 prevents flow past the stop and into the port 1545 unless the tubing is expanded away from the stop sufficiently to form the flow channel. This may be accomplished by an increase in pressure in the tubing sufficient to expand the tubing radially, or by pressing on the tubing to open a flow path around the stop or occluder 1540. As shown in FIG. 37, the occluder 1540 may include one or more annular ribs 1547 to facilitate sealing with the interior of the tubing. It will be appreciated that the occluder 1540 can be placed in other positions along the pump tubing segment 1510 or even extending into the inflow line 1525 or the outflow line 1530.

Figure 24:
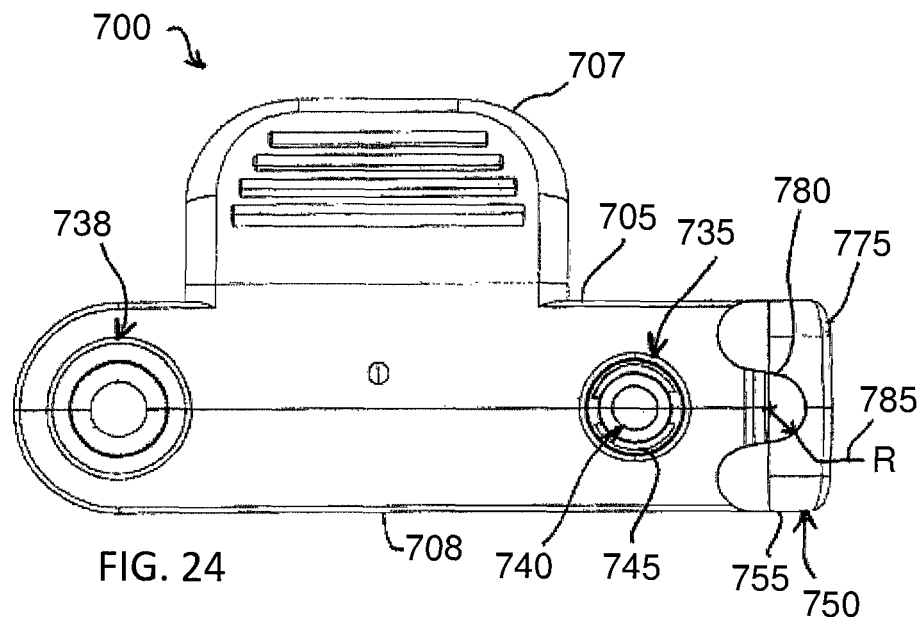
FIGS. 24 and 25 are rotated and enlarged opposite end views of the cassette body depicted in FIG. 14 and FIGS. 17 through 23.
Figure 25:
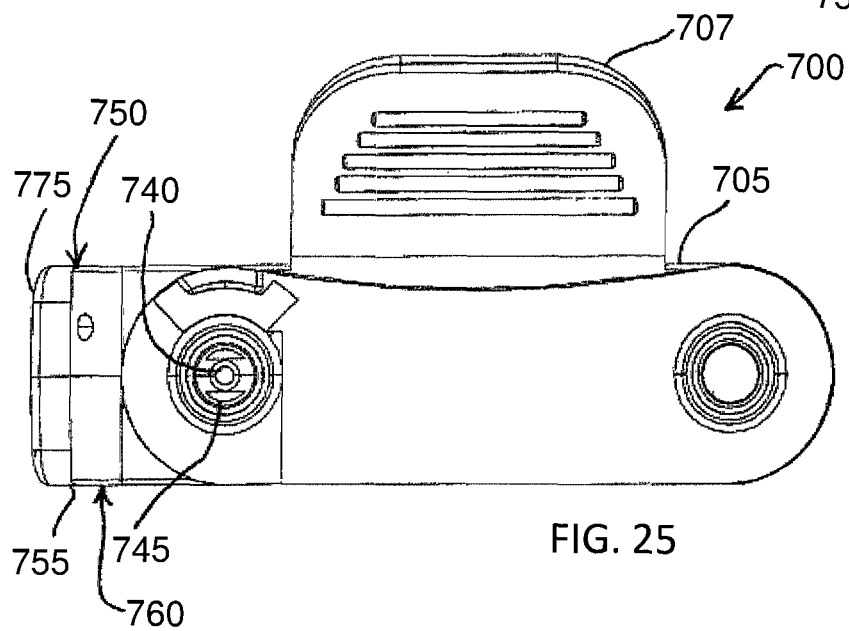
Figure 26:
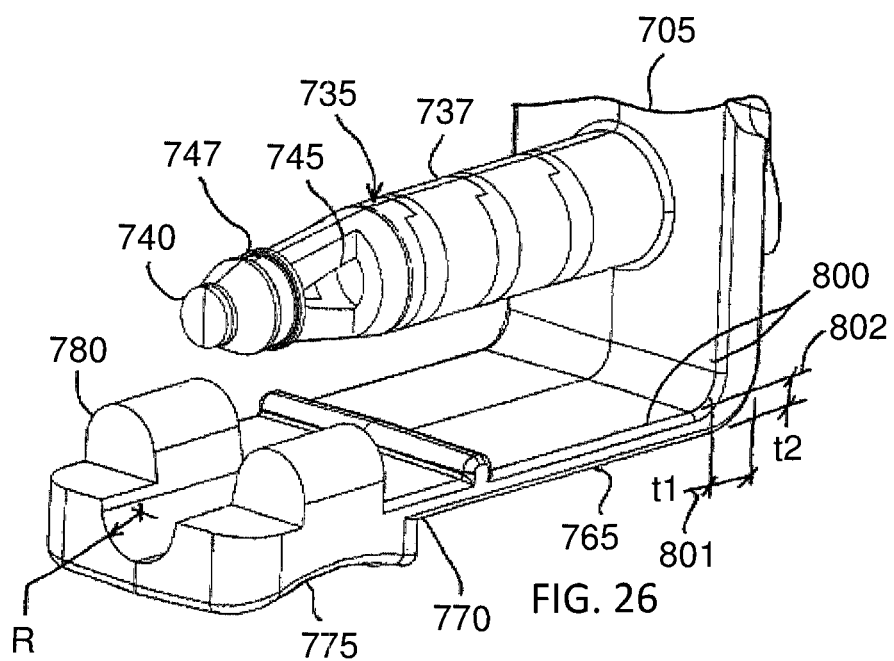
FIG. 26 is an enlarged isometric rotated view of a portion of the cassette body of FIG. 14 and FIGS. 17 through 25.
Figure 27:
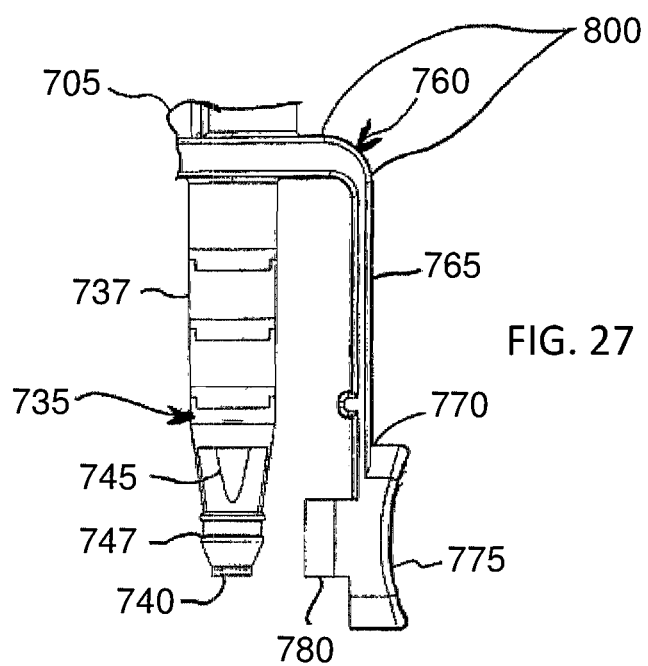
FIG. 27 is another enlarged rotated view of the portion of the cassette body shown in FIG. 26.

The recess 1585 in the engagement member 1555 may be formed to define a radius, R, (FIG. 38) along at least a portion thereof that is about the same size and preferably slightly narrower than the outer diameter of the tubing segment, and more preferably narrower than the outer diameter of the occluder. The projections 1580 or similar structure may be broadly rounded as shown in FIGS. 8B, 9B and 24, may form a deep channel as shown in FIG. 24 and/or may have relatively sharp edges as shown in FIG. 38. In each case, the projections 1580 or similar structures of the engagement member 1555 are able to engage the tubing segment 1540 sufficiently to distend or deform the tubing over the occluder 1540 and open the flow channel past the occluder to allow fluid flow through the lumen.

Those skilled in the art will appreciate that the actuator 1550 can be actuated from a rest position to a deflected or actuated position similar to that shown in FIG. 29 with relatively little effort. In the deflected or actuated position, the projections 1580 and walls of the channel 1585 formed by the engagement member 1555 are urged into contact with the pump tubing segment 1510 similar to that shown in FIG. 29. While shown disposed on the bottom in FIGS. 37 and 38, the actuator 1550 may be disposed at any orientation about tubing.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

In use, the various embodiments discussed above have an inflow end of the tubing segment which is connected to a liquid source, typically by an inflow tube. The liquid source may be a chemical solution when used in a laboratory, or an enteral feeding solution or an IV solution in a medical context. The outflow tubing extends to a point of delivery which may be a test tube in a laboratory context or a patient in the context of enteral or parenteral solution delivery. A user typically then primes the enteral feeding set by depressing the actuator and then mounts the cassette body or carrier of the feeding set on the mounting plate or similar structure of a pump system. Thereafter the pump controller subsystem is actuated to effect feeding of the enteral liquid to the patient.

When used with a rotary pump, the peristalsis loop is pulled over the rotor prior to mounting the cassette body in the mounting structure. In contrast, in a linear or curvilinear pump, one of the cassette bodies is mounted on one side of the pumping mechanism and the tubing segment is drawn across the pumping mechanism. The other cassette body is then mounted on the mounting structure of the pump so that the tube is in tension adjacent the pumping mechanism.

The embodiments of the present invention are suitable for use in many applications that involve manufacture, sale, and use of peristaltic pumping systems generally and which may have particularly beneficial applications in enteral and parenteral solution delivery to patients in a medical context. The embodiments can be used to provide delivery sets and/or to allow flow with the delivery set attached to a pump.

The configurations of the inventive enteral delivery systems may be modified to accommodate many types of enteral feeding sets and the like that are suitable for use in healthcare facilities as well as in home care environments. Such feeding sets may be adapted with various types of tubing to accommodate a variety of enterally deliverable, liquid nutritional products, parenterally deliverable hydration or medication, etc., which may have various viscosities and consistencies.

Such modifications and alternative arrangements may be configured to establish compatibility with the wide variety of possible applications that are susceptible for use with the inventive and improved delivery sets and feeding sets 698 for delivering the contemplated liquid nutritional products. Accordingly, even though only few such embodiments, alternatives, variations, and modifications of the present invention are described and illustrated herein, it should be understood that the practice of such additional modifications and variations, and the equivalents thereof, are within the spirit and scope of the invention as defined in the following claims.

Thus there are disclosed embodiments of anti-free-flow mechanisms, cassettes embodying anti-free-flow mechanisms and associated methods of use, and other enhancements to a cassette used with a peristaltic pump. Those skilled in the art will appreciate numerous modifications which can be made in light of the present disclosure that do not depart from the scope of the invention. The appended claims are intended to cover such modifications.

What is claimed is:

1. A cassette for mounting on a peristaltic pump housing, the cassette comprising:
    a cassette body having at least one connector, the at least one connector including an occluder;
    a flexible pump tube attached to the at least one connector; and
    an angled engagement surface disposed on the cassette body at least partially disposed on a projection extending from the body and being disposed at an angle relative to the body, the angled engagement surface engaging the peristaltic pump housing such that the cassette body is removably mountable on the peristaltic pump housing;
    wherein the angled engagement surface interacts with a complimentary surface of the peristaltic pump housing such that under tension from partial engagement of the complimentary surface, the cassette body is biased into a mounted position;
    wherein the engagement surface comprises a first sloped section and a second sloped section;
    wherein the second sloped section is disposed at substantially the same angle as the first sloped section and is disposed further away from the body than the first sloped section;
    wherein the occluder is disposed in a portion of the flexible pump tube to selectively prevent flow therethrough.

2. The cassette of claim 1, wherein the engagement surface comprises a third sloped section between the first sloped section and the second sloped section, the third sloped section being at a different angle than the first sloped section or the second sloped section.

3. The cassette of claim 1, wherein the engagement surface has at least a portion thereof disposed at an angle of about 3 to about 15 degrees relative to the body member.

4. The cassette of claim 1, wherein the engagement surface is disposed at an angle of about 10 degrees or less relative to the body.

5. The cassette of claim 1, wherein the engagement surface comprises a third surface portion generally perpendicular to the first sloped section and the second sloped section.

6. The cassette of claim 5, wherein the first and second sloped sections are disposed at an angle of about 15 degrees or less relative to the body member.

7. The cassette of claim 1, wherein the engagement surface is disposed on the same side of the body as the tube, and wherein loading the cassette in a pump places the tube in tension and biases the engagement surfaces into contact with a mounting structure on a pump.

8. A cassette for a fluid delivery set, the cassette comprising:
    a tubing segment;
    an occluder disposed in a portion of the tubing segment to selectively prevent flow therethrough;
    a cassette body connected to the tubing segment, the cassette body having a projection extending therefrom, at least a portion of the projection being disposed adjacent the portion of the tubing containing the connector occluder, the projection being movable between a first position wherein the projection does not forcefully engage the tubing to distend the tubing adjacent the occluder to thereby open a flow channel between the portion of the tubing and the occluder and a second position wherein at least a portion of the projection forcefully engages the tubing and distends the tubing to open at least one flow path between the tubing and the occluder;
    wherein the cassette body is configured to be removably mountable to a peristaltic pump housing.

9. The cassette of claim 8, wherein the cassette body includes a connector and wherein the occluder is attached to and spaced apart from the connector to form a fluid flow port.

10. The cassette of claim 8, wherein the projection has an engagement member disposed along the projection for engaging the portion of the tubing section.

11. The cassette of claim 10, wherein the engagement member includes a plurality of rounded projections for engaging the portion of the tubing segment.

12. The cassette of claim 11 wherein the occluder has a radius and wherein engagement member includes a recess between the projections, at least a portion of the recess having a radius which is the same or smaller than the radius of the occluder.

13. A device for selectively preventing flow through an infusion set, the device comprising:
- an occluder having at least one body, the at least one body forming a stop for disposition in a tubing segment to selectively prevent flow therethrough and the at least one body forming an actuator, the actuator being deflectable to forcefully engage the tubing segment to open a flow channel past the occluder, the actuator extending from the body to a position adjacent the stop;
- wherein the device is configured to be removably mountable to a peristaltic pump housing;
- wherein the actuator comprises an engagement member for engaging and deforming the tubing segment.

14. A fluid delivery set comprising the device of claim 13, the fluid delivery set comprising a tubing segment, the stop being disposed in the tubing segment and the actuator extending along the occluder segment.

15. The fluid delivery set according to claim 14, wherein the at least one body comprises a first body comprising the stop and a second body comprising the actuator.

16. The fluid delivery set according to claim 15, wherein the first body is attached to the second body by at least one of the group consisting of press-fit, snap fit, bonding or adhesive.

17. The fluid delivery set according to claim 14, wherein the body comprises at least one projection having an angled face configured for engaging a recess on a peristaltic pump.

18. A fluid delivery system including the fluid delivery set of claim 17, wherein the pump comprises a recess having an angled surface for complementary receipt of the angled face of the projection of the body.

19. The fluid delivery system of claim 18, wherein the projection has an angled face disposed at 0 to 15 degrees from vertical and wherein the recess has an angled engagement surface which is disposed at 0 to 15 degrees in the opposite direction.

20. A fluid delivery cassette comprising:
- a cassette body having a first connector and a second connector, at least one of the connectors having an occluder attached thereto;
- a tubing segment attached to the first connector and the second connector, the occluder being disposed in the tubing segment; and
- an actuator extending from the cassette body to a position on the outside of the tubing segment adjacent the occluder, the actuator being deflectable to forcefully engage the tubing segment with the occluder to open a flow channel past the occluder;
- wherein the cassette body is configured to be removably mountable to a peristaltic pump housing.

21. A fluid delivery cassette of claim 20, wherein the actuator comprises a bendable arm.

22. The fluid delivery cassette of claim 21, further comprising an engagement member disposed on the bendable arm for engaging and deforming the tubing segment.

* * * * *